(12) United States Patent
Shiraiwa et al.

(10) Patent No.: US 11,396,613 B2
(45) Date of Patent: Jul. 26, 2022

(54) CURED PRODUCT, OPTICAL MEMBER, LENS, AND COMPOUND

(71) Applicant: FUJIFILM Corporation, Tokyo (JP)

(72) Inventors: Naozumi Shiraiwa, Kanagawa (JP); Naoyuki Morooka, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 17/006,996

(22) Filed: Aug. 31, 2020

(65) Prior Publication Data

US 2021/0017315 A1 Jan. 21, 2021

Related U.S. Application Data

(63) Continuation of application No. PCT/JP2019/010133, filed on Mar. 13, 2019.

(30) Foreign Application Priority Data

Mar. 14, 2018 (JP) .............................. JP2018-046342

(51) Int. Cl.
| | |
|---|---|
| *C07D 239/72* | (2006.01) |
| *C07D 239/74* | (2006.01) |
| *C07D 241/42* | (2006.01) |
| *C07D 241/44* | (2006.01) |
| *C09D 133/14* | (2006.01) |
| *C08F 220/30* | (2006.01) |
| *C08F 222/10* | (2006.01) |

(52) U.S. Cl.
CPC ......... *C09D 133/14* (2013.01); *C07D 239/72* (2013.01); *C07D 239/74* (2013.01); *C07D 241/42* (2013.01); *C07D 241/44* (2013.01); *C08F 220/301* (2020.02); *C08F 220/302* (2020.02); *C08F 222/1025* (2020.02)

(58) Field of Classification Search
CPC .. C07D 133/14; C07D 239/72; C07D 239/74; C07D 241/42; C07D 241/44
See application file for complete search history.

(56) References Cited

U.S. PATENT DOCUMENTS

| | | |
|---|---|---|
| 2013/0237630 A1 | 9/2013 | Morooka et al. |
| 2015/0175731 A1 | 6/2015 | Saitoh |
| 2017/0009138 A1 | 1/2017 | Nakazawa et al. |
| 2017/0174992 A1 | 6/2017 | Ootsuki |
| 2018/0305486 A1 | 10/2018 | Nakayama et al. |

FOREIGN PATENT DOCUMENTS

| | | |
|---|---|---|
| CN | 106977527 A | 7/2017 |
| JP | 10-307399 A | 11/1998 |
| JP | 2006-241048 A | 9/2006 |
| JP | 2009-126011 A | 6/2009 |
| JP | 2010-59242 A | 3/2010 |
| JP | 2012-107191 A | 6/2012 |
| JP | 2014-043565 A | 3/2014 |
| JP | 2014-194411 A | 10/2014 |
| JP | 2016-053149 A | 4/2016 |
| JP | 2017-125009 A | 7/2017 |
| WO | 2017/115649 A1 | 7/2017 |

OTHER PUBLICATIONS

Silver et al. "Poly(methyl methacrylate) copolymers containing dipyrrolylquinoxaline receptors for the colorimetric detection of halide anion salts", Supramolecular Chemistry, vol. 24, No. 2, Feb. 2012, pp. 101-105.

Wan et al., "Ratiometric Fluorescence Detection of Phosphorylated Amino Acids Through Excited-State Proton Transfer by Using Molecularly Imprinted Polymer (MIP) Recognition Nanolayers", Sensor Particles, Chemistry—A European Journal, vol. 23, 2017, pp. 15974-15983.

Beldi et al., "Efficient Diverse Approach for Quinoxaline-Derived Glycosylated and Morphinylated Analogs", *J. Heterocyclic Chem.*, vol. 48, 2011, pp. 50-56.

Kawai et al., 8-dioxy quinoxaline—diallyl ether (II), Nippon kagaku zassi, vol. 80, No. 7, Jul. 10, 1959, p. 806 (2 pages).

Braun et al., "Photoinduzierte Polymerisation von Methylmethacrylat in Gegenwart von niederund hochmolekularen Chinoxalinderivaten", Die Angewandte Makromolekulare Chemie, vol. 43, 1975, pp. 125-143.

(Continued)

*Primary Examiner* — Bruck Kifle
(74) *Attorney, Agent, or Firm* — Sughrue Mion, PLLC

(57) ABSTRACT

The present invention provides a cured product obtained by curing a curable composition including a compound represented by General Formula 1, in which a birefringence Δn (587 nm) is 0.00≤Δn (587 nm)≤0.01.

$$Pol_1\text{-}Sp_1\text{-}L_1\text{-}Ar\text{-}L_2\text{-}Sp_2\text{-}Pol_2 \qquad \text{(General Formula 1)}$$

In the formula, Ar represents a divalent group containing a ring structure selected from the group consisting of a quinoxaline ring and a quinazoline ring; $L_1$ and $L_2$ each represent a single bond, —O—, —OC(=O)—, —OC(=O)O—, —OC(=O)NH—, and the like; $Sp_1$ and $Sp_2$ each represent a single bond or a divalent linking group; $Pol_1$ and $Pol_2$ each represent a hydrogen atom or a polymerizable group; and the compound represented by General Formula 1 has at least one polymerizable group. The cured product of the present invention has a small Abbe number (vd) and a large partial dispersion ratio (θg, F), and is therefore useful for production of optical members.

10 Claims, No Drawings

(56) References Cited

OTHER PUBLICATIONS

Sasse, et al. "2.3-Disubstituierte Chinoxaline, eine Gruppe neuer Pflanzenschutzmittel", Angewandte Chemie, vol. 72,1960, pp. 973-981.
International Search Report dated Jun. 11, 2019 from the International Searching Authority in International Application No. PCT/JP2019/010133.
Written Opinion dated Jun. 11, 2019 from the International Bureau in International Application No. PCT/JP2019/010133.
International Preliminary Report on Patentability dated Sep. 15, 2020 from the International Bureau in International Application No. PCT/JP2019/010133.
Office Action dated May 11, 2021, issued by the Japanese Patent Office in Japanese application No. 2020-506578.

CURED PRODUCT, OPTICAL MEMBER, LENS, AND COMPOUND

CROSS-REFERENCE TO RELATED APPLICATIONS

This application is a continuation of PCT International Application No. PCT/JP2019/010133 filed on Mar. 13, 2019, which claims priority under 35 U.S.C § 119 (a) to Japanese Patent Application No. 2018-046342 filed on Mar. 14, 2018, the entire content of which is incorporated herein by reference.

BACKGROUND OF THE INVENTION

1. Field of the Invention

The present invention relates to a cured product, an optical member, a lens, and a compound.

2. Description of the Related Art

In the related art, glass materials have been used for an optical member of an imaging module such as a camera, a video camera, a mobile phone with a camera, a video phone, or a door phone with a camera. Glass materials have been used preferably because they have various optical characteristics and excellent environmental resistance, but they have a disadvantage in that weight reduction and miniaturization are not easy and workability and productivity are poor. In contrast, resin cured products can be produced in a massive amount and have excellent workability, and therefore they have recently been used in various optical members.

In recent years, a size of an optical member used in an imaging module is required to be reduced in accordance with miniaturization of the imaging module, but in a case of miniaturizing an optical member, a problem of chromatic aberrations occurs. In an optical member formed of a resin cured product, studies have been conducted regarding adjusting an Abbe number by adding various additives to a curable composition to change characteristics after curing, and thereby correcting chromatic aberrations.

For example, JP2014-043565A discloses that, using a 4,4'-bis(aryl)diphenylsulfone skeleton monomer, it is possible to provide a molded article having a large Abbe number (vd), a large partial dispersion ratio (θg, F), and a low birefringence index, which are characteristics of an excellent chromatic aberration correction performance; an optical element; and an optical composition for obtaining the molded article.

Meanwhile, JP2017-125009A discloses a liquid crystal monomer having a quinoxaline ring group or a quinazoline ring group.

SUMMARY OF THE INVENTION

An object of the present invention is to provide a cured product having a small Abbe number (vd) and a large partial dispersion ratio (θg, F) for manufacturing an optical member. In particular, an object of the present invention is to provide a cured product which has a partial dispersion ratio larger than that of the cured product disclosed in JP2014-043565A, and which does not exhibit birefringent properties as those of the cured product disclosed in JP2017-125009A. Another object of the present invention is to provide a highly functional optical member and lens.

The inventors of the present invention have diligently studied to achieve the above-described objects, and have found that, by using a compound having a quinoxaline ring group or a quinazoline ring group, it is possible to obtain a cured product having a small Abbe number and a large partial dispersion ratio.

That is, the present invention provides the following <1> to <15>.

<1> A cured product obtained by curing a curable composition including a compound represented by General Formula 1, in which a birefringence Δn at a wavelength of 587 nm is $0.00 \leq \Delta n \leq 0.01$.

$$\text{Pol}_1\text{-Sp}_1\text{-L}_1\text{-Ar-L}_2\text{-Sp}_2\text{-Pol}_2 \quad \text{(General Formula 1)}$$

In the formula, Ar represents a divalent group containing a ring structure selected from the group consisting of a quinoxaline ring and a quinazoline ring, $L_1$ and $L_2$ each independently represent a single bond, or a linking group selected from the group consisting of —O—, —S—, —C(=O)—, —OC(=O)—, —C(=O)O—, —OC(=O)O—, —NR$_{101}$C(=O)—, —C(=O)NR$_{102}$—, —OC(=O)NR$_{103}$—, —NR$_{104}$C(=O)—, —SC(=O)—, and —C(=O)S—, where $R_{101}$, $R_{102}$, $R_{103}$, and $R_{104}$ each independently represent -Sp$_3$-Pol$_3$ or a halogen atom, $Sp_1$, $Sp_2$, and $Sp_3$ each independently represent a single bond or a divalent linking group, $Pol_1$, $Pol_2$, and $Pol_3$ each independently represent a hydrogen atom or a polymerizable group, and the compound represented by General Formula 1 has at least one polymerizable group.

<2> The cured product according to <1>, in which Ar is any group represented by General Formulas 2-1 to 2-5.

(2-1)

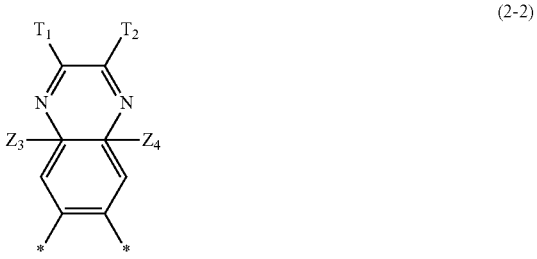

(2-2)

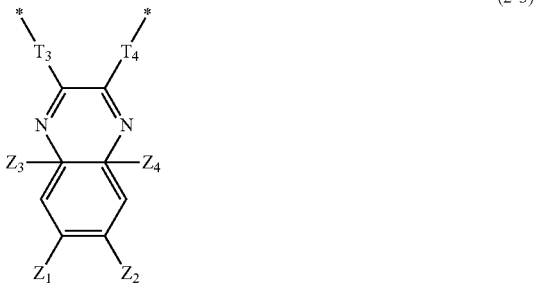

(2-3)

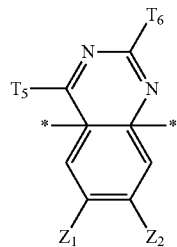

(2-4)

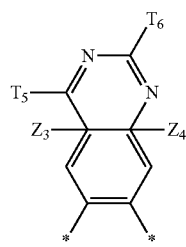

(2-5)

In General Formulas 2-1 to 2-5, $Z_1$, $Z_2$, $Z_3$, and $Z_4$ each independently represent a hydrogen atom, an aliphatic hydrocarbon group which has 1 to 20 carbon atoms and may have a substituent, an alkoxy group which has 1 to 20 carbon atoms and may have a substituent, an alkoxycarbonyl group which has 1 to 20 carbon atoms and may have a substituent, an alicyclic hydrocarbon group which has 3 to 20 carbon atoms and may have a substituent, an aromatic hydrocarbon group which has 6 to 20 carbon atoms and may have a substituent, a halogen atom, a cyano group, a nitro group, —$NR_{12}R_{13}$, $SR_{12}$, or an aromatic heterocyclic ring which may have a substituent, and $Z_1$ and $Z_2$ may be bonded to each other to form an aromatic hydrocarbon ring which may have a substituent or an aromatic heterocyclic ring which may have a substituent, where $R_{12}$ and $R_{13}$ each independently represent a hydrogen atom, or an alkyl group which has 1 to 6 carbon atoms and may have a substituent, $T_1$, $T_2$, $T_5$, and $T_6$ each independently represent a halogen atom, a cyano group, a nitro group, -L-$Sp_6$-$Pol_6$, an alicyclic hydrocarbon group which has 3 to 20 carbon atoms and may have a substituent, an aromatic hydrocarbon group which has 6 to 20 carbon atoms and may have a substituent, an aromatic heterocyclic group which may have a substituent, $NR_{12}R_{13}$, or $SR_{12}$, and $T_1$ and $T_2$ may be bonded to each other to form an aromatic hydrocarbon ring which may have a substituent or an aromatic heterocyclic ring which may have a substituent, $L_6$ is synonymous with $L_1$, $Sp_6$ represents a single bond, or a linking group selected from the group consisting of a linear alkylene group which has 1 to 30 carbon atoms and may have a substituent and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S— in the linear alkylene group which has 1 to 30 carbon atoms and may have a substituent, where $R_{201}$, $R_{202}$, $R_{203}$, and $R_{204}$ each independently represent -$Sp_4$-$Pol_4$ or a halogen atom, $Sp_4$ represents a single bond or a divalent linking group, $Pol_4$ and $Pol_6$ are each independently synonymous with $Pol_1$, and $T_3$ and $T_4$ each independently represent a divalent aromatic hydrocarbon group which has 6 to 12 carbon atoms and may have a substituent or a divalent aromatic heterocyclic group which may have a substituent.

<3> The cured product according to <2>, in which Ar is any group represented by General Formulas 2-1 to 2-3.

<4> The cured product according to any one of <1> to <3>, in which $Sp_1$ and $Sp_2$ each independently represent a single bond, or a linking group selected from the group consisting of a linear alkylene group which has 1 to 30 carbon atoms and may have a substituent and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S— in the linear alkylene group which has 1 to 30 carbon atoms and may have a substituent, where $R_{201}$, $R_{202}$, $R_{203}$, and $R_{204}$ each independently represent -$Sp_4$-$Pol_4$ or a halogen atom, $Sp_4$ represents a single bond or a divalent linking group, $Pol_4$ represents a hydrogen atom or a poymerizable group.

<5> The cured product according to any one of <1> to <4>, in which both $L_1$ and $L_2$ are —O—, —OC(=O)—, —OC(=O)O—, or —O—C(=O)NH—.

<6> The cured product according to any one of <1> to <5>, in which all the polymerizable groups are (meth)acryloyloxy groups.

<7> The cured product according to any one of <1> to <6>, in which $Pol_1$-$Sp_1$-$L_1$- and $Pol_2$-$Sp_2$-$L_2$- are the same.

<8> An optical member comprising the cured product according to any one of <1> to <7>.

<9> A lens comprising the cured product according to any one of <1> to <7>.

<10> A compound represented by General Formula 1.

$Pol_1$-$Sp_1$-$L_1$-Ar-$L_2$-$Sp_2$-$Pol_2$ (General Formula 1)

In the formula, Ar represents a divalent group containing a ring structure selected from the group consisting of a quinoxaline ring and a quinazoline ring, $L_1$ and $L_2$ each independently represent a single bond, or a linking group selected from the group consisting of —O—, —S—, —C(=O)—, —C(=O)—, —C(=O)O—, —OC(=O)O—, —$NR_{101}$C(=O)—, —C(=O)$NR_{102}$—, —OC(=O)$NR_{103}$—, —$NR_{104}$C(=O)O—, —SC(=O)—, and —C(=O)S—, where $R_{101}$, $R_{102}$, $R_{101}$, and $R_{104}$ each independently represent -$Sp_3$-$Pol_3$ or a halogen atom, $Sp_1$ and $Sp_2$ each independently represent a single bond, or a linking group selected from the group consisting of a linear alkylene group which has 1 to 30 carbon atoms and may have a substituent and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S— in the linear alkylene group which has 1 to 30 carbon atoms and may have a substituent, where $R_{201}$, $R_{202}$, $R_{203}$, and $R_{204}$ each independently represent -$Sp_4$-$Pol_4$ or a halogen atom, $Sp_3$ and $Sp_4$ each independently represent a single bond or a divalent linking group, $Pol_1$, $Pol_2$, $Pol_3$, and $Pol_4$ each independently represent a hydrogen atom or a polymerizable group, and the compound represented by General Formula 1 has at least one polymerizable group.

<11> The compound according to <10>, in which Ar is any group represented by General Formulas 2-1 to 2-5.

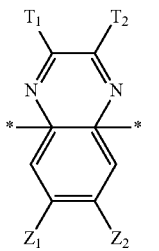

(2-1)

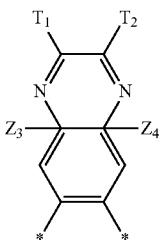

(2-2)

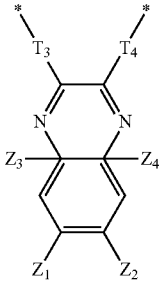

(2-3)

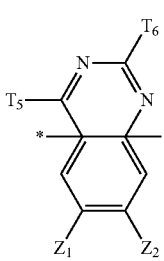

(2-4)

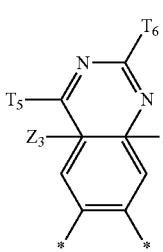

(2-5)

In General Formulas 2-1 to 2-5, $Z_1$, $Z_2$, $Z_3$, and $Z_4$ each independently represent a hydrogen atom, an aliphatic hydrocarbon group which has 1 to 20 carbon atoms and may have a substituent, an alkoxy group which has 1 to 20 carbon atoms and may have a substituent, an alkoxycarbonyl group which has 1 to 20 carbon atoms and may have a substituent, an alicyclic hydrocarbon group which has 3 to 20 carbon atoms and may have a substituent, an aromatic hydrocarbon group which has 6 to 20 carbon atoms and may have a substituent, a halogen atom, a cyano group, a nitro group, —$NR_{12}R_{13}$, $SR_{12}$, or an aromatic heterocyclic ring which may have a substituent, and $Z_1$ and $Z_2$ may be bonded to each other to form an aromatic hydrocarbon ring which may have a substituent or an aromatic heterocyclic ring which may have a substituent, where $R_{12}$ and $R_{13}$ each independently represent a hydrogen atom, or an alkyl group which has 1 to 6 carbon atoms and may have a substituent, $T_1$, $T_2$, $T_5$, and $T_6$ each independently represent a halogen atom, a cyano group, a nitro group, -$L_6$-$Sp_6$-$Pol_6$, an alicyclic hydrocarbon group which has 3 to 20 carbon atoms and may have a substituent, an aromatic hydrocarbon group which has 6 to 20 carbon atoms and may have a substituent, an aromatic heterocyclic group which may have a substituent, $NR_{12}R_{13}$, or $SR_{12}$, and $T_1$ and $T_2$ may be bonded to each other to form an aromatic hydrocarbon ring which may have a substituent or an aromatic heterocyclic ring which may have a substituent, $L_6$ is synonymous with $L_1$, $Sp_6$ represents a single bond, or a linking group selected from the group consisting of a linear alkylene group which has 1 to 30 carbon atoms and may have a substituent and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S— in the linear alkylene group which has 1 to 30 carbon atoms and may have a substituent, where $R_{201}$, $R_{202}$, $R_{203}$, and $R_{204}$ each independently represent -$Sp_4$-$Pol_4$ or a halogen atom, $Sp_4$ represents a single bond or a divalent linking group, $Pol_4$ and $Pol_6$ are each independently synonymous with $Pol_1$, and $T_3$ and $T_4$ each independently represent a divalent aromatic hydrocarbon group which has 6 to 12 carbon atoms and may have a substituent or a divalent aromatic heterocyclic group which may have a substituent.

<12> The compound according to <11>, in which Ar is any group represented by General Formulas 2-1 to 2-3.

<13> The compound according to <11> or <12>, in which both $L_1$ and $L_2$ are —O—, —OC(=O)—, —OC(=O)O—, or —O—C(=O)NH—.

<14> The compound according to any one of <10> to <13>, in which $Pol_1$-$Sp_1$-$L_1$- and $Pol_2$-$Sp_2$-$L_2$- are the same.

<15> The compound according to any one of <10> to <14>, in which all the polymerizable groups are (meth)acryloyloxy groups.

According to the present invention, a cured product having a small Abbe number (vd) and a large partial dispersion ratio (θg, F) is provided. Using the cured product of the present invention, it is possible to provide a highly functional optical member and lens. In addition, according to the present invention, a novel compound that can provide the cured product having a small Abbe number (vd) and a large partial dispersion ratio (θg, F) is provided.

DESCRIPTION OF THE PREFERRED EMBODIMENTS

Hereinafter, the present invention will be described in detail. The description of constituent elements described below can be made based on representative embodiments and specific examples, but the present invention is not limited to such embodiments. Numerical ranges expressed using "to" in the present specification mean a range including numerical values described before and after "to" as the lower limit and the upper limit.

In the present specification, "(meth)acrylate" refers to any one or both of acrylate and methacrylate, and "(meth)acryloyl" refers to any one or both of acryloyl and methacryloyl. The monomer in the present invention is a compound distinguished from oligomers and polymers and having a weight-average molecular weight of 1,000 or less.

<Cured Product>

A cured product of the embodiment of the present invention is formed from a curable composition containing a compound represented by General Formula 1. The cured product of the embodiment of the present invention is obtained by polymerization of the compound represented by General Formula 1, but the cured product of the embodiment of the present invention may include an unreacted compound represented by General Formula 1.

The compound represented by General Formula 1 contains a quinoxaline ring or a quinazoline ring in a structure thereof. The inventors of the present invention have found that the cured product formed from the curable composition containing the compound represented by General Formula 1 has a small Abbe number (vd) and a large partial dispersion ratio (θg, F). Because the above-mentioned compound has absorption in a near ultraviolet region, it is considered to exhibit anomalous dispersibility of refractive index, thereby improving a chromatic aberration correction performance in a case of being used as a compound lens. The inventors of the present invention have further found that the cured product formed from the curable composition containing the compound represented by General Formula 1 has a small change in refractive index due to a wet heat environment.

An Abbe number (vd) and a partial dispersion ratio (θg, F) of the cured product are values measured using a Kalnew precision refractometer KPR-2000 (manufactured by Shimadzu Device Corporation). Specifically, the curable composition is poured into a transparent glass mold having a diameter of 20 mm and a thickness of 2 mm, and heated at 200° C. in an atmosphere having an oxygen concentration of 1% or less to form a cured product (a heating step), and an Abbe number (vd) and a partial dispersion ratio (θg, F) of this cured product are measured. The Abbe number (vd) and the partial dispersion ratio (θg, F) of the cured product are calculated by the following formula. In a case of molding a cured product, an ultraviolet irradiation step may be employed instead of the above-described heating step, or both of the heating step and the ultraviolet irradiation step may be employed.

$$vd=(nd-1)/(nF-nC)$$

$$\theta g, F=(ng-nF)/(nF-nC)$$

Where nd represents a refractive index at a wavelength of 587.56 nm, nF represents a refractive index at a wavelength of 486.13 nm, nC represents a refractive index at a wavelength of 656.27 nm, and ng represents a refractive index at a wavelength of 435.83 nm.

The Abbe number of the cured product of the embodiment of the present invention is not particularly limited, but is preferably 35 or less, more preferably 30 or less, even more preferably 29 or less, and particularly preferably 28 or less. In addition, the Abbe number of the cured product of the embodiment of the present invention is not particularly limited, but it is preferably 1 or more, is more preferably 3 or more, is even more preferably 5 or more, and is particularly preferably 7 or more.

The partial dispersion ratio (θg, F) of the cured product of the embodiment of the present invention is not particularly limited, but it is preferably 0.65 or more, is more preferably 0.70 or more, and is even more preferably 0.75 or more. In addition, the partial dispersion ratio (θg, F) of the cured product of the embodiment of the present invention is not particularly limited, but it is preferably 2 or less, is more preferably 1.8 or less, and is even more preferably 1.7 or less.

A birefringence Δn at a wavelength of 587 nm of the cured product of the embodiment of the present invention (in the present specification, sometimes referred to as a birefringence Δn (587 nm)) is 0.00≤Δn≤0.01. The birefringence Δn (587 nm) is preferably 0.001 or less and is more preferably less than 0.001. By using a cured product having such a low birefringence index for an optical member of an imaging module, it is possible to obtain a clear image in which an imaging position is unlikely to shift. The lower limit value of the birefringence Δn (587 nm) may be 0.00001 or 0.0001.

The birefringence Δn (587 nm) of the cured product can be obtained by the following method. A film-like sample is produced, and using a birefringence evaluation apparatus (for example, WPA-100, manufactured by Photonic Lattice, Inc.), a birefringence within a 10 mm diameter circle including the center of the sample is measured, an average value of birefringence at a wavelength of 587 nm is obtained, and thereby a birefringence Δn (587 nm) can be obtained.

(Compound Represented by General Formula (1))

The cured product of the embodiment of the present invention is obtained by curing a curable composition containing a compound represented by General Formula 1.

   (General Formula 1)

In the formula, Ar represents a divalent group containing a ring structure selected from the group consisting of a quinoxaline ring and a quinazoline ring, $L_1$ and $L_2$ each independently represent a single bond, or a linking group selected from the group consisting of —O—, —S—, —C(=O)—, —OC(=O)—, —C(=O)O—, —OC(=O)O—, —NR$_{101}$C(=O)—, —C(=O)NR$_{102}$—, —OC(=O)NR$_{103}$—, —NR$_{104}$C(=O)O—, —SC(=O)—, and —C(=O)S—, where $R_{101}$, $R_{102}$, $R_{103}$, and $R_{104}$ each independently represent -Sp$_3$-Pol$_3$ or a halogen atom, $Sp_1$, $Sp_2$, and $Sp_3$ each independently represent a single bond or a divalent linking group, $Pol_1$, $Pol_2$, and $Pol_3$ each independently represent a hydrogen atom or a polymerizable group, and the compound represented by General Formula 1 has at least one polymerizable group.

Hereinafter, each substituent will be described.

In the present specification, in a case where an aliphatic hydrocarbon group is referred to, it represents a group obtained by removing one hydrogen atom from a linear or branched alkane, a linear or branched alkene, or a linear or branched alkyne. In the present specification, the aliphatic hydrocarbon group is preferably an alkyl group obtained by removing any one of hydrogen atoms from a linear or branched alkane. Examples of alkyl groups include a methyl group, an ethyl group, a propyl group, an isopropyl group, a butyl group, an isobutyl group, a sec-butyl group, a tert-butyl group, a pentyl group, a 1-methylbutyl group, a 3-methylbutyl group, a hexyl group, a 1-methylpentyl group, a 4-methylpentyl group, a heptyl group, a 1-methylhexyl group, a 5-methylhexyl group, an octyl group, a 1-methylheptyl group, a nonyl group, a 1-methyloctyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and the like.

The aliphatic hydrocarbon group (unsubstituted) is preferably an alkyl group having 1 to 12 carbon atoms, and is particularly preferably a methyl group or an ethyl group.

In the present specification, in a case where an alkyl group is referred to, it represents a linear or branched alkyl group. Examples of alkyl groups include the above-mentioned examples. The same applies to an alkyl group in groups (for example, an alkoxy group, an alkoxycarbonyl group, and the like) containing an alkyl group.

In addition, in the present specification, examples of linear alkylene groups include groups obtained by removing each hydrogen atom bonded to a terminal carbon from a linear alkyl group among the above-mentioned alkyl groups.

In the present specification, in a case where an alicyclic hydrocarbon group is referred to, it represents a cycloalkyl group obtained by removing any one of hydrogen atoms from cycloalkane. Examples of alicyclic hydrocarbon groups include a cyclopropyl group, a cyclobutyl group, a cyclopentyl group, a cyclohexyl group, a cycloheptyl group, a cyclooctyl group, a cyclononyl group, a cyclodecyl group, and the like, where a cycloalkyl group having 3 to 12 carbon atoms is preferable.

In the present specification, the aromatic hydrocarbon ring means an aromatic ring forming a ring only with carbon atoms. The aromatic hydrocarbon ring may be a single ring or a fused ring. An aromatic hydrocarbon ring having 6 to 14 carbon atoms is preferable. Examples of aromatic hydrocarbon rings include benzene, naphthylene, anthracene, phenanthrene, and the like. In the present specification, in a case where an aromatic hydrocarbon ring is bonded to another ring, it is sufficient for the aromatic hydrocarbon ring be substituted by the other ring as a monovalent or divalent aromatic hydrocarbon group.

In the present specification, in a case where a monovalent group is referred to regarding an aromatic hydrocarbon group, it represents a monovalent group obtained by removing any one of hydrogen atoms from an aromatic hydrocarbon ring. The monovalent aromatic hydrocarbon group is preferably an aromatic hydrocarbon group having 6 to 14 carbon atoms. Examples thereof include a phenyl group, a biphenyl group, a 1-naphthyl group, a 2-naphthyl group, a 1-anthracenyl group, a 2-anthracenyl group, a 3-anthracenyl group, a 4-anthracenyl group, a 9-anthracenyl group, a 1-phenanthryl group, a 2-phenanthryl group, a 3-phenanthryl group, a 4-phenanthryl group, a 9-phenanthryl group, and the like. Among the examples, a phenyl group is preferable.

In the present specification, in a case where a divalent group is referred to regarding an aromatic hydrocarbon group, it represents a divalent group obtained by removing any one of hydrogen atoms from the above-mentioned monovalent aromatic hydrocarbon group. Examples of divalent aromatic hydrocarbon groups include a phenylene group, a biphenylene group, a naphthylene group, a phenanthrylene group, and the like, where a phenylene group is preferable, and a 1,4-phenylene group is more preferable.

In the present specification, the aromatic heterocyclic ring means an aromatic ring in which a ring is formed by carbon atoms and heteroatoms. Examples of heteroatoms include an oxygen atom, a nitrogen atom, a sulfur atom, and the like. The aromatic heterocyclic ring may be a single ring or a fused ring, and the number of elements constituting the ring is preferably 5 to 20, and more preferably 5 to 14. The number of heteroatoms in the elements constituting the ring is not particularly limited, but it is preferably 1 to 3 and is more preferably 1 to 2. Examples of aromatic heterocyclic rings include furan, thiophene, pyrrole, imidazole, isothiazole, isoxazole, pyridine, pyrazine, quinoline, and the like. In the present specification, in a case where an aromatic heterocyclic ring is bonded to another ring, it is sufficient for the aromatic heterocyclic ring be substituted by the other ring as a monovalent or divalent aromatic heterocyclic group.

In the present specification, in a case where a monovalent group is referred to regarding an aromatic heterocyclic group, it represents a monovalent group obtained by removing any one of hydrogen atoms from an aromatic heterocyclic ring. Examples of monovalent aromatic heterocyclic groups include a furyl group, a thienyl group, a pyrrolyl group, an imidazolyl group, an isothiazolyl group, an isoxazolyl group, a pyridyl group, a pyrazinyl group, a quinolyl group, and the like. Among the examples, a furyl group and a thienyl group are preferable, and a 2-furyl group and a 2-thienyl group are more preferable.

In General Formula 1, examples of the divalent group which is represented by Ar and contains a ring structure selected from the group consisting of a quinoxaline ring and a quinazoline ring include a divalent group consisting of a quinoxaline ring which may have a substituent and a divalent group consisting of a quinazoline ring which may have a substituent. Positions of bonds of these divalent groups are not particularly limited, and it is sufficient for two positions be selected from the group consisting of any carbon atom on a quinoxaline ring or a quinazoline ring, and any atom (preferably carbon atoms) in a substituent substituting for the quinoxaline ring or the quinazoline ring. Among the examples, positions is preferably two positions selected from the group consisting of any carbon atom on a quinoxaline ring or a quinazoline ring, or two positions selected from the group consisting of any atom in a substituent.

Positions of bonds on a quinoxaline ring or a quinazoline ring are not particularly limited, but they are preferably two positions selected from 5-position to 8-position, and are more preferably 5-position and 8-position, or 6-position and 7-position.

In a case where a bond is on a substituent substituting for a quinoxaline ring or a quinazoline ring, the substituent is preferably an aromatic hydrocarbon group or an aromatic heterocyclic group which may have a substituent, is more preferably an aromatic hydrocarbon group which has 6 to 12 carbon atoms and may have a substituent, is even more preferably a phenyl group which may have a substituent (a phenylene group which may have a substituent as a state having a bond), and is particularly preferably a phenyl group (a phenylene group as a state having a bond). In a case where a phenyl group has a bond, a position thereof is preferably at a 4-position (where a bonding position to a quinoxaline ring or a quinazoline ring is a 1-position) (that is, a 1,4-phenylene group).

Ar preferably contains a structure in which one or two groups selected from the group consisting of an aromatic hydrocarbon ring which may have a substituent and an aromatic heterocyclic ring which may have a substituent are directly bonded to a quinoxaline ring or a quinazoline ring, more preferably contains a structure in which one or two groups selected from the group consisting of aromatic hydrocarbon rings which have 6 to 12 carbon atoms which may have a substituent are directly bonded to a quinoxaline ring or a quinazoline ring, and even more preferably contains a structure in which one or two benzene rings are directly bonded to a quinoxaline ring or a quinazoline ring.

Ar is preferably any group represented by General Formulas 2-1 to 2-5.

(2-1) 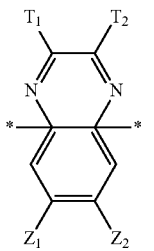

(2-2) 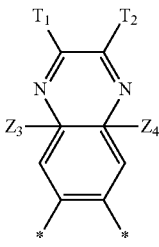

(2-3) 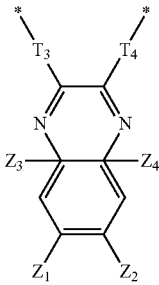

(2-4) 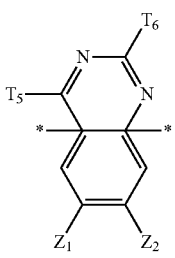

(2-5) 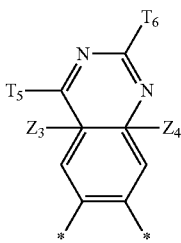

In General Formulas 2-1 to 2-5, $Z_1$, $Z_2$, $Z_3$, and $Z_4$ represent monovalent groups, and each independently represent a hydrogen atom, an aliphatic hydrocarbon group which has 1 to 20 carbon atoms and may have a substituent, an alkoxy group which has 1 to 20 carbon atoms and may have a substituent, an alkoxycarbonyl group which has 1 to 20 carbon atoms and may have a substituent, an alicyclic hydrocarbon group which has 3 to 20 carbon atoms and may have a substituent, an aromatic hydrocarbon group which has 6 to 20 carbon atoms and may have a substituent, a halogen atom, a cyano group, a nitro group, —$NR_{12}R_{13}$, or $SR_{12}$, or an aromatic heterocyclic group which may have a substituent, where $Z_1$ and $Z_2$ may be bonded to each other to form an aromatic hydrocarbon ring which may have a substituent or an aromatic heterocyclic ring which may have a substituent, and $R_{12}$ and $R_{13}$ each independently represent a hydrogen atom, or an alkyl group which has 1 to 6 carbon atoms and may have a substituent.

In the description of the respective substituents in General Formulas 2-1 to 2-5, a substituent in a case where the phrase "may have a substituent" is referred to is not particularly limited as long as the substituent is not highly desorbable (easily decomposable) such as an acid chloride (—COCl) or -OTf (—O—$SO_2CF_3$). Examples thereof include a halogen atom (for example, a fluorine atom, a chlorine atom, and a bromine atom), a hydroxy group, an amino group, a cyano group, a nitro group, a nitroso group, a carboxy group, an alkyl group having 1 to 6 carbon atoms, an alkoxy group having 1 to 6 carbon atoms, an alkoxycarbonyl group having 1 to 6 carbon atoms, an alkylcarbonyloxy group having 1 to 6 carbon atoms, an alkylcarbonyl group having 1 to 6 carbon atoms, an alkylsulfinyl group having 1 to 6 carbon atoms, an alkylsulfonyl group having 1 to 6 carbon atoms, a fluoroalkyl group having 1 to 6 carbon atoms, an alkylsulfanyl group having 1 to 6 carbon atoms, an N-alkylamino group having 1 to 6 carbon atoms, an N,N-dialkylamino group having 2 to 12 carbon atoms, an N-alkylsulfamoyl group having 1 to 6 carbon atoms, an N,N-dialkylsulfamoyl group having 2 to 12 carbon atoms, and the like. Among these substituents, a halogen atom, a hydroxy group, an alkyl group having 1 to 6 carbon atoms, an alkoxy group having 1 to 6 carbon atoms, and a fluoroalkyl group having 1 to 6 carbon atoms are preferable, and a fluorine atom, a chlorine atom, a bromine atom, a hydroxy group, a methyl group, a methoxy group, and a fluoromethyl group are more preferable.

It is preferable that $Z_1$ and $Z_2$ be each independently a hydrogen atom or an aliphatic hydrocarbon group which has 1 to 20 carbon atoms and may have a substituent, or $Z_1$ and $Z_2$ are bonded to each other to form an aromatic hydrocarbon ring which may have a substituent. It is more preferable that $Z_1$ and $Z_2$ be each independently a hydrogen atom or a methyl group, or $Z_1$ and $Z_2$ are bonded to each other to form a benzene ring.

It is preferable that $Z_3$ and $Z_4$ be each independently a hydrogen atom or an aliphatic hydrocarbon group having 1 to 20 carbon atoms which may have a substituent, and it is more preferable that $Z_3$ and $Z_4$ be each independently a hydrogen atom or a methyl group.

In General Formulas 2-1 and 2-2 and General Formulas 2-4 and 2-5, $T_1$, $T_2$, $T_5$, and $T_6$ represent monovalent groups and each independently represent a halogen atom, a cyano group, a nitro group, -$L_6$-$Sp_6$-$Pol_6$, an alicyclic hydrocarbon group which has 3 to 20 carbon atoms and may have a substituent, an aromatic hydrocarbon group which has 6 to 20 carbon atoms and may have a substituent, an aromatic heterocyclic group which may have a substituent, $NR_{12}R_{13}$, or $SR_{12}$.

$L_6$ is synonymous with $L_1$, but the left side is bonded to a quinoxaline ring or a quinazoline ring, and the right side is bonded to $Sp_6$ in the description of a linking group to be exemplified. L is preferably a single bond, —O—, —OC(=O)—, or —C(=O)O—, and is more preferably a single bond.

$Sp_6$ is a single bond, or a linking group selected from the group consisting of a linear alkylene group which has 1 to 30 carbon atoms and may have a substituent, and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)NR$_{202}$—, —OC(=O)NR$_{203}$—, —NR$_{204}$C(=O)O—, —SC(=O)—, or —C(=O)S— in the linear alkylene group which has 1 to 30 carbon atoms and may have a substituent. R$_{201}$, R$_{202}$, R$_{203}$, and R$_{204}$ each independently represent -Sp$_4$-Pol$_4$ or a halogen atom; Sp$_4$ represents a single bond or a divalent linking group; and Pol$_4$ and Pol$_6$ are each independently synonymous with Pol$_1$.

Sp$_6$ is preferably a linking group selected from the group consisting of a linear alkylene group which has 1 to 10 carbon atoms and may have a substituent, and a group in which one or two or more non-adjacent —CH$_2$—'s are substituted by —O—, —C(=O)—, —OC(=O)—, —C(=O)O—, or —OC(=O)O— in the linear alkylene group which has 1 to 10 carbon atoms and may have a substituent.

Examples of polymerizable groups represented by Pol$_6$ include the same polymerizable groups as those for Pol$_1$ to be described later, and a preferable range of polymerizable groups is also the same. A hydrogen atom is preferable as Pol$_6$.

Examples of -L$_6$-Sp$_6$-Pol$_6$ include a hydrogen atom, the following examples as a group represented by -L$_1$-Sp$_1$-Pol$_1$, and a group selected from the group consisting of an aliphatic group which has 1 to 20 carbon atoms and may have a substituent and an alkoxy group which has 1 to 20 carbon atoms and may have a substituent, or a group having a polymerizable group at the end of these groups.

It is preferable that T$_1$ and T$_2$ be each independently an aromatic hydrocarbon group which has 6 to 20 carbon atoms and may have a substituent, an aromatic heterocyclic group which may have a substituent, an aliphatic hydrocarbon group which has 1 to 20 carbon atoms and may have a substituent, or the following examples as the group represented by -L$_1$-Sp$_1$-Pol$_1$. It is more preferable that T$_1$ and T$_2$ be each independently a phenyl group which may have a substituent, a biphenyl group, a naphthyl group, an alkyl group having 1 to 6 carbon atoms, a furyl group, or a thienyl group. It is even more preferable that T$_1$ and T$_2$ be each independently a phenyl group, a 4-biphenyl group, a 1-naphthyl group, a 2-naphthyl group, an alkyl group having 1 to 6 carbon atoms, a 2-furyl group, or a 2-thienyl group. It is particularly preferable that T$_1$ and T$_2$ be each independently a phenyl group.

T$_1$ and T$_2$ may be the same as or different from each other, but they are preferably the same as each other. However, it is also preferable that one of T$_1$ and T$_2$ be a phenyl group which may have a substituent and the other be a hydrogen atom or an alkyl group having 1 to 4 carbon atoms.

At least one of T$_1$ or T$_2$ is preferably not a hydrogen atom. In addition, at least one of T$_1$ or T$_2$ is preferably an aromatic hydrocarbon group which has 6 to 20 carbon atoms and may have a substituent, or an aromatic heterocyclic group which may have a substituent.

T$_1$ and T$_2$ may be bonded to each other to form an aromatic hydrocarbon ring which may have a substituent or an aromatic heterocyclic ring which may have a substituent. In this case, T$_1$ and T$_2$ are preferably bonded to each other to form an aromatic hydrocarbon ring which may have a substituent, are more preferably bonded to each other to form benzene which may have a substituent, naphthylene which may have a substituent, anthracene which may have a substituent, or phenanthrene which may have a substituent, and are even more preferably bonded to each other to form benzene or phenanthrene.

It is preferable that T$_5$ and T$_6$ be each independently an aromatic hydrocarbon group which has 6 to 20 carbon atoms and may have a substituent, an aromatic heterocyclic group which may have a substituent, an aliphatic hydrocarbon group which has 1 to 20 carbon atoms and may have a substituent, or the following examples as the group represented by -L$_1$-Sp$_1$-Pol$_1$. It is more preferable that T$_1$ and T$_2$ be each independently a hydrogen atom, a phenyl group which may have a substituent, a biphenyl group, a naphthyl group, an alkyl group having 1 to 6 carbon atoms, a fury group, or a thienyl group. It is even more preferable that T$_1$ and T$_2$ be each independently a hydrogen atom, a phenyl group, a 4-biphenyl group, a 1-naphthyl group, a 2-naphthyl group, an alkyl group having 1 to 6 carbon atoms, a 2-furyl group, or a 2-thienyl group. It is particularly preferable that T$_1$ and T$_2$ be each independently a hydrogen atom or a phenyl group.

T$_5$ and T$_6$ may be the same as or different from each other. It is also preferable that T$_6$ be any of the above-mentioned preferable substituents and T$_5$ be a hydrogen atom.

At least one of T$_5$ or T$_6$ is preferably not a hydrogen atom. In addition, at least one of T$_5$ or T$_6$ is preferably an aromatic hydrocarbon group which has 6 to 20 carbon atoms and may have a substituent, or an aromatic heterocyclic group which may have a substituent.

In General Formula 2-3, T$_3$ and T$_4$ represent divalent linking groups, and each independently represent a divalent aromatic hydrocarbon group which has 6 to 12 carbon atoms and may have a substituent or a divalent aromatic heterocyclic group which may have a substituent. As T$_3$ and T$_4$, a divalent aromatic hydrocarbon group which has 6 to 12 carbon atoms and may have a substituent is preferable, a divalent aromatic hydrocarbon group having 6 to 10 carbon atoms is more preferable, a phenylene group is even more preferable, and a 1,4-phenylene group is particularly preferable.

T$_3$ and T$_4$ may be the same as or different from each other, but they are preferably the same as each other.

Ar in General Formula 1 is more preferably any group represented by General Formulas 2-1 to 2-3. The reason for this is because then, synthesis is easy and raw materials can be obtained at low costs.

In General Formula 1, L$_1$ and L$_2$ each independently represent a single bond, or a linking group selected from the group consisting of —O—, —S—, —C(=O)—, —OC(=O)—, —C(=O)O—, —OC(=O)O—, —NR$_{101}$C(=O)—, —C(=O)NR$_{102}$—, —OC(=O)NR$_{103}$—, —NR$_{104}$C(=O)O—, —SC(=O)—, and C(=O)S—. In the description of the above-mentioned linking group, the left side is bonded to Ar, and the right side is bonded to Sp$_1$ or Sp$_2$. R$_{101}$, R$_{102}$, R$_{103}$, and R$_{104}$ each independently represent -Sp$_3$-Pol$_3$ or a halogen atom. L$_1$ and L$_2$ each independently preferably are —O—, —OC(=O)—, —C(=O)O—, —OC(=O)O—, —NR$_{101}$C(=O)—, —C(=O)NR$_{102}$—, —OC(=O)NR$_{103}$—, or —NR$_{104}$C(=O)O—, more preferably are —O—, —OC(=O)—, —OC(=O)O—, or —OC(=O)NR$_{103}$, and even more preferably are —O—. R$_{101}$, R$_{102}$, R$_{103}$, and R$_{104}$ each independently preferably are a hydrogen atom, an alkyl group having 1 to 4 carbon atoms, or a halogen atom.

L$_1$ and L$_2$ may be the same as or different from each other, but they are preferably the same as each other.

Sp$_1$, Sp$_2$, and Sp$_3$ each independently represent a single bond or a divalent linking group. Examples of divalent linking groups include the following linking groups, and linking groups selected from the group consisting of two or more combinations of the following linking groups.

Examples of Sp$_1$, Sp$_2$, and Sp$_3$ which are divalent linking groups include a linking group in which a linear alkylene group that may have a substituent, a cycloalkylene group that may have a substituent, a divalent aromatic hydrocarbon group that may have a substituent, and a divalent aromatic heterocyclic group that may have a substituent are bonded to two or more linking groups which are selected from the group consisting of a linear alkylene group that may have a substituent, a cycloalkylene group that may have a substituent, a divalent aromatic ring group that may have a substituent, and a divalent aromatic heterocyclic group that may have a substituent, via a linking group selected from a single bond, —O—, —S—, —C(=O)—, —OC(=O)—, —C(=O)O—, —OC(=O)O—, —NR$_{201}$C(=O)—, —C(=O)NR$_{202}$—, —OC(=O)NR$_{203}$—, —NR$_{204}$C(=O)O—, —SC(=O)—, and —C(=O)S—; and the like.

Preferable examples of $Sp_1$, $Sp_2$, and $Sp_3$ which are divalent linking groups include a linking group in which a linear alkylene group that may have a substituent, a cycloalkylene group that may have a substituent, and a divalent aromatic hydrocarbon group that may have a substituent are bonded to two or more linking groups which are selected from the group consisting of a linear alkylene group that may have a substituent, a cycloalkylene group that may have a substituent, and a divalent aromatic ring group that may have a substituent, via a linking group selected from a single bond, —O—, —C(=O)—, —OC(=O)—, —C(=O)O—, —OC(=O)O—, —NR$_{201}$C(=O)—, and —C(=O)NR$_{202}$—; and the like.

In the description of the linking group, the left side is bonded to $L_1$, $L_2$, or N (in the case of $Sp_3$), and the right side is bonded to $Pol_1$, $Pol_2$, or $Pol_3$.

$R_{201}$, $R_{202}$, $R_{203}$, and $R_{204}$ each independently represent -$Sp_4$-$Pol_4$ or a halogen atom. $Sp_4$ and $Pol_4$ each are synonymous with $Sp_3$ and $Pol_3$, and their preferable ranges are also the same. $R_{201}$, $R_{202}$, $R_{203}$, and $R_{204}$ each independently preferably are a hydrogen atom, an alkyl group having 1 to 4 carbon atoms, or a halogen atom.

A substituent referred to in the case of referring to the phrase "may have a substituent" regarding the substituents in $Sp_1$, $Sp_2$, and $Sp_3$, and General Formulas 2-1 to 2-4 is not particularly limited as long as the substituent is not highly desorbable (easily decomposable) such as an acid chloride (—COCl) or -OTf (—O—SO$_2$CF$_3$). Examples thereof include an alkyl group, a cycloalkyl group, an alkoxy group, an acyl group, an acyloxy group, an alkoxycarbonyl group, an amide group, an amino group, a halogen atom, a nitro group, and a cyano group, and a substituent selected from the group consisting of groups composed of a combination of two or more substituents among the above-mentioned substituents. The substituent may be a group represented by -$Sp_5$-$Pol_5$. $Sp_5$ and $Pol_5$ each are synonymous with $Sp_1$ and $Pol_1$, and their preferable ranges are also the same. The number of substituents is not particularly limited, and 1 to 4 substituents may be present. In a case where there are two or more substituents, the two or more substituents may be the same as or different from each other.

It is preferable that the divalent linking groups represented by $Sp_1$ and $Sp_2$ each independently represent a linking group selected from the group consisting of a linear alkylene group which has 1 to 30 carbon atoms and may have a substituent and a group in which one or two or more non-adjacent —CH$_2$—'s are substituted by —O—, —S—, —C(=O)—, —OC(=O)—, —C(=O)O—, —OC(=O)O—, —NR$_{201}$C(=O)—, —C(=O)NR$_{202}$—, —OC(=O)NR$_{203}$—, —NR$_{204}$C(=O)O—, —SC(=O)—, or —C(=O)S— in the linear alkylene group which has 1 to 30 carbon atoms and may have a substituent. As described above, by using a compound in which $Sp_1$ and $Sp_2$ are linking groups not having a cyclic group in the main chain, the birefringence Δn (587 nm) of the cured product is easily adjusted to 0.00≤Δn (587 nm)≤0.01.

$Sp_1$ and $Sp_2$ may be the same as or different from each other, but they are preferably the same.

In $Sp_1$ and $Sp_2$, in a case where —CH$_2$— is substituted with other divalent groups selected from the group consisting of —O—, —S—, —C(=O)—, —OC(=O)—, —C(=O)O—, —OC(=O)O—, —NR$_{201}$C(=O)—, —C(=O)NR$_{202}$—, —OC(=O)NR$_{203}$—, —NR$_{204}$C(=O)O—, —SC(=O)—, and —C(=O)S— in a linear alkylene group having 1 to 30 carbon atoms, it is preferable that the other substituted divalent group be not directly bonded to $L_1$ or $L_2$. That is, a site substituted by the other divalent group is preferably not an $L_1$ side terminal of $Sp_1$, and an $L_2$ side terminal of $Sp_2$.

It is more preferable that the divalent linking groups represented by $Sp_1$ and $Sp_2$ each independently represent a linking group selected from the group consisting of groups in which one or two or more non-adjacent —CH$_2$—'s are substituted by —O—, —C(=O)—, —OC(=O)—, —C(=O)O—, —OC(=O)O—, —NR$_{201}$C(=O)—, —C(=O)NR$_{202}$—, —OC(=O)NR$_{203}$—, or —NR$_{204}$C(=O)O— in a linear alkylene group which has 1 to 20 carbon atoms and may have a substituent, and the linear alkylene group which has 1 to 20 carbon atoms and may have a substituent. It is even more preferable that the divalent linking groups represented by $Sp_1$ and $Sp_2$ each independently represent a linking group selected from the group consisting of groups in which one or two or more non-adjacent —CH$_2$—'s are substituted by —O—, —C(=O)—, —OC(=O)—, or —C(=O)O— in a linear alkylene group which has 1 to 10 carbon atoms and may have a substituent, and the linear alkylene group which has 1 to 10 carbon atoms and may have a substituent. It is particularly preferable that the divalent linking groups represented by $Sp_1$ and $Sp_2$ each independently represent a linking group selected from the group consisting of groups in which one or two or more non-adjacent —CH$_2$—'s are substituted by —O—, —C(=O)—, —OC(=O)—, or —C(=O)O— in a linear alkylene group which has 1 to 10 carbon atoms and which has no substituent or has a methyl group as a substituent, and the linear alkylene group which has 1 to 10 carbon atoms and which has no substituent or has a methyl group as a substituent.

The divalent linking group represented by $Sp_3$ is preferably a single bond or a linear alkylene group which has 1 to 10 carbon atoms and may have a substituent, is more preferably a linear alkylene group which has 1 to 5 carbon atoms and may have a substituent, is even more preferably a linear alkylene group which has 1 to 3 carbon atoms and may have a substituent, and is particularly preferably an unsubstituted linear alkylene group.

$Pol_1$, $Pol_2$, and $Pol_3$ each independently represent a hydrogen atom or a polymerizable group. Examples of polymerizable groups include polymerizable groups represented by Formulas Pol-1 to Pol-6.

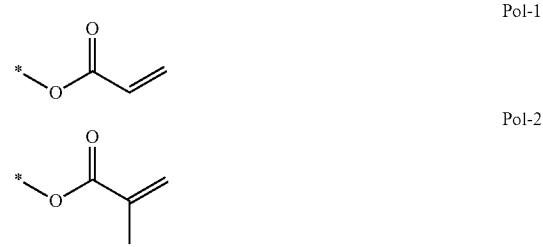

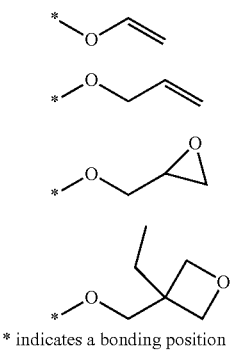

* indicates a bonding position

Among them, (meth)acryloyloxy groups (Pol-1, Pol-2) are preferable.

It is preferable that any one of the polymerizable groups $Pol_1$ or $Pol_2$ be a (meth)acryloyloxy group, and it is more preferable that both be (meth)acryloyloxy groups.

$Pol_1$ and $Pol_2$ may be the same as or different from each other, but they are preferably the same.

The compound represented by General Formula 1 has at least one polymerizable group. The compound represented by General Formula 1 preferably has at least two polymerizable groups.

It is preferable that -$Sp_3$-$Pol_3$ and -$Sp_4$-$Pol_4$ be each independently a hydrogen atom or a substituted or unsubstituted alkyl group having 1 to 4 carbon atoms. It is more preferable that -$Sp_3$-$Pol_3$ and -$Sp_4$-$Pol_4$ be each independently a hydrogen atom or an unsubstituted alkyl group having 1 to 4 carbon atoms.

Examples of specific structures of $Pol$-$Sp_1$-$L_1$- or $Pol_2$-$Sp_2$-$L_2$- include the following structures.

$Pol_1$-$Sp_1$-$L_1$- or $Pol_2$-$Sp_2$-$L_2$- may be the same as or different from each other, but they are preferably the same.

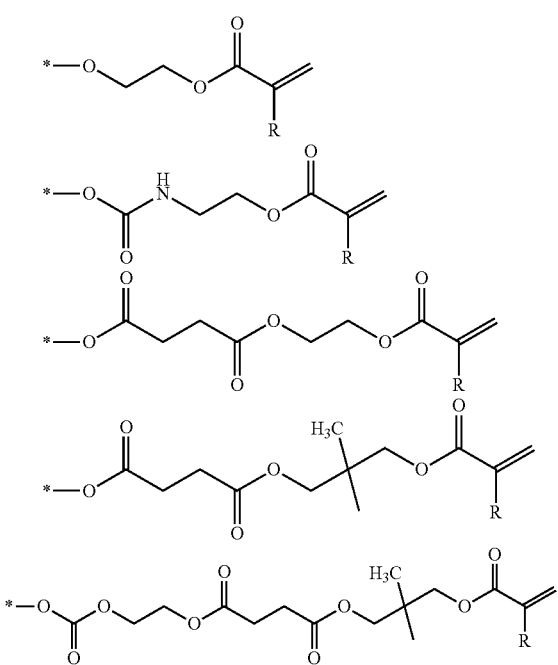

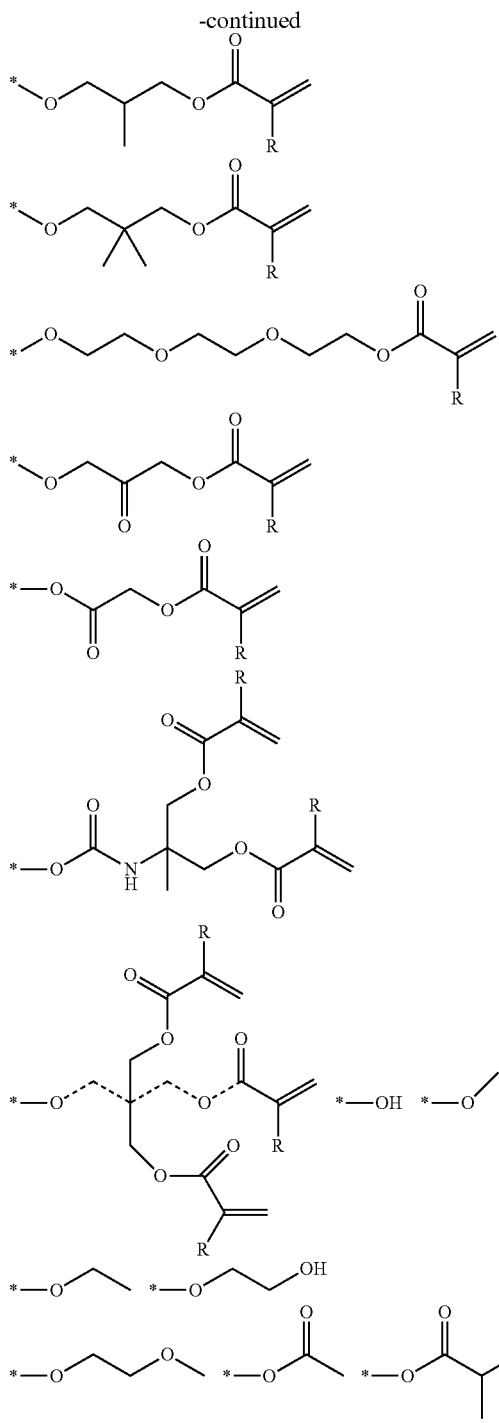

(R is a hydrogen atom or a methyl group, and * indicates a bonding position with Ar)

In the present specification, the following structure shows mixture of two partial structures of which methyl groups are respectively bonded to any one carbon of an ethylene group.

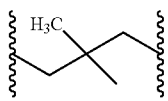 [SMILES: *CC(C)(C)C*]

As described above, in a case where the compound represented by General Formula 1 has a structure in which a substituent is substituted on a linear alkylene group, structural isomers having different substitution positions of the substituent may be present. The compound represented by General Formula 1 may be a mixture of such structural isomers.

The compound represented by General Formula 1 is preferably a non-liquid crystalline compound.

Specific examples of the compound represented by General Formula 1 which is preferably used in the curable composition of the present invention are listed below, but the compounds are not limited to the following compounds. In the following structural formulas, Me represents a methyl group, Et represents an ethyl group, iPr represents an i-propyl group, nPr represents an n-propyl group, nBu represents an n-butyl group, and tBu represents a t-butyl group.

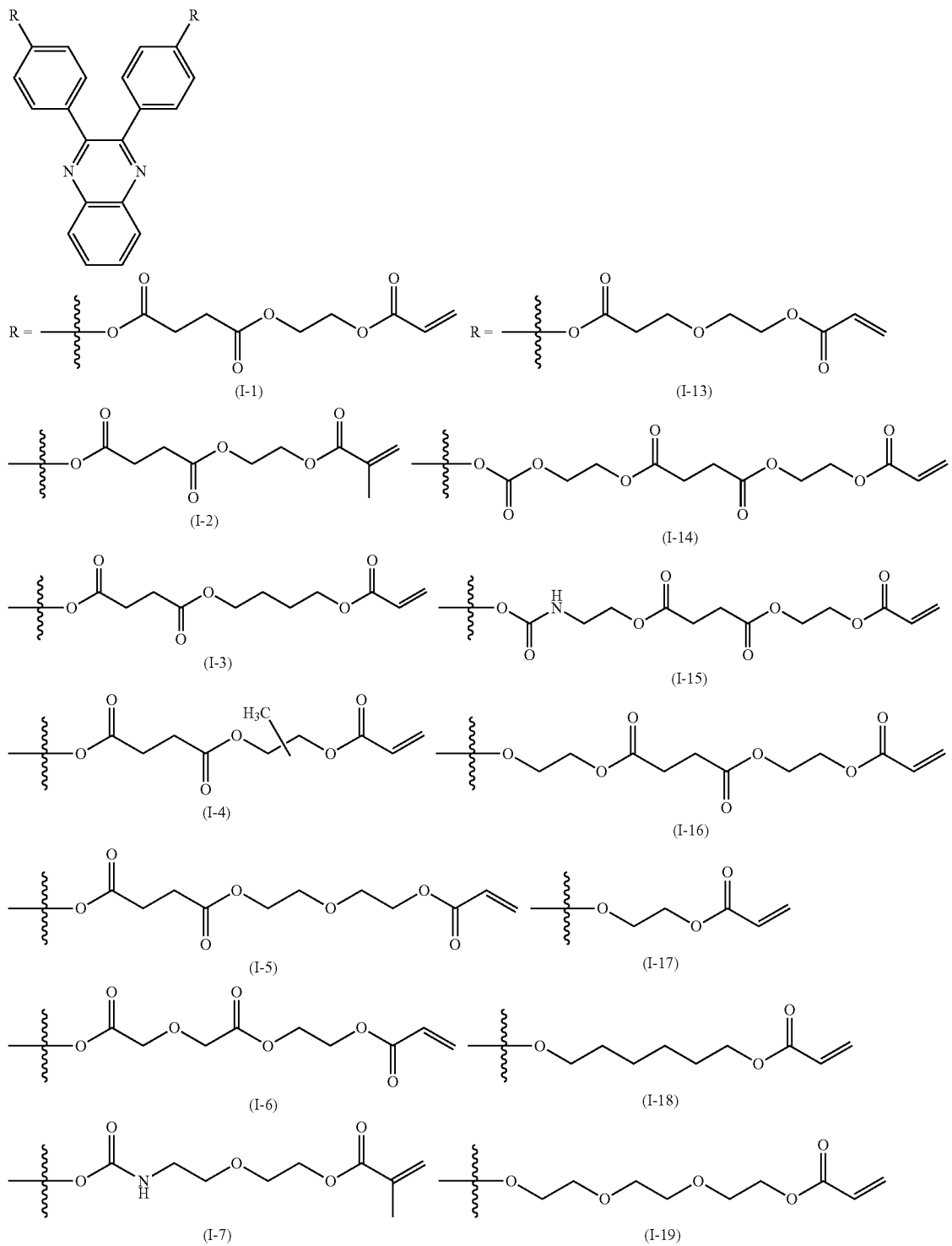

-continued
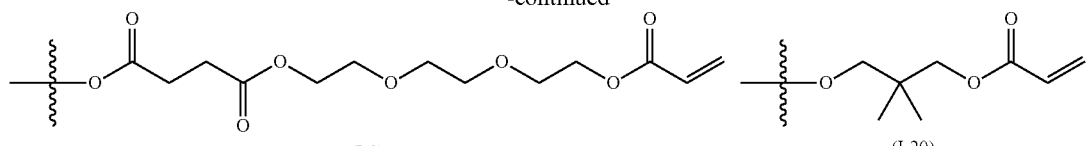
(I-8) (I-20)
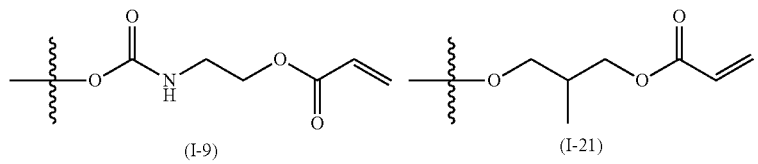
(I-9) (I-21)
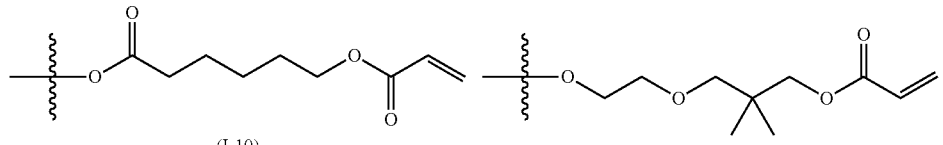
(I-10) (I-22)
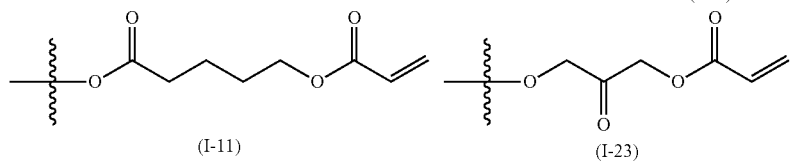
(I-11) (I-23)
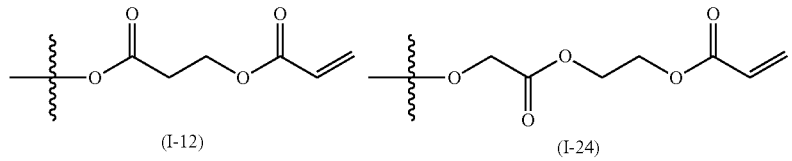
(I-12) (I-24)
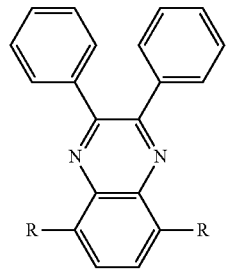
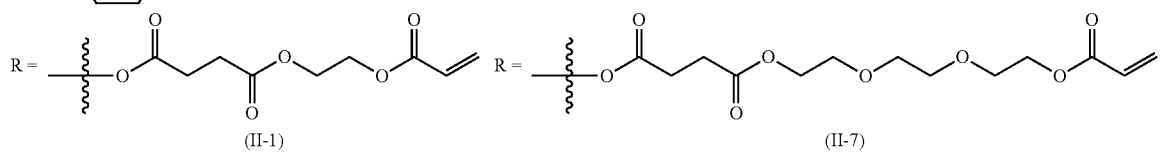
(II-1) (II-7)
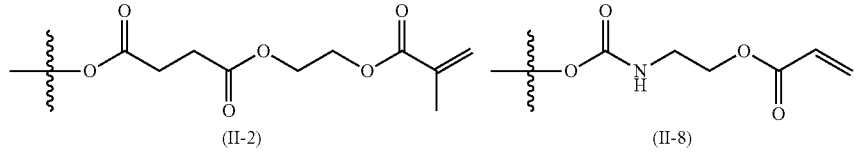
(II-2) (II-8)
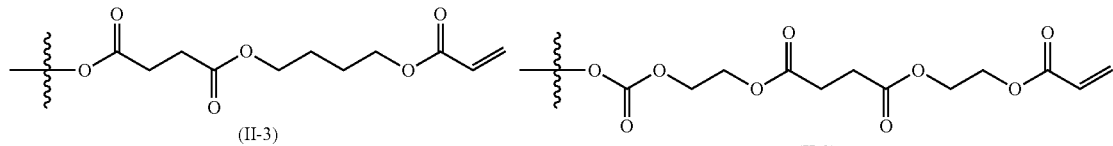
(II-3) (II-9)
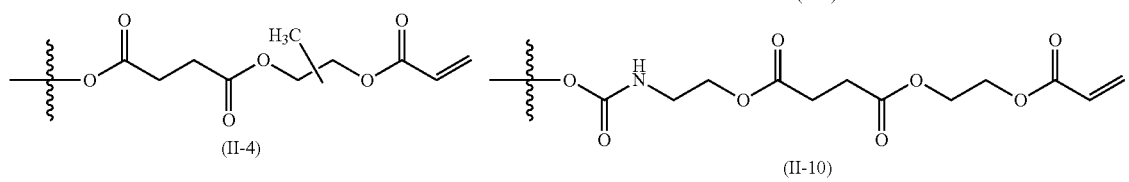
(II-4) (II-10)

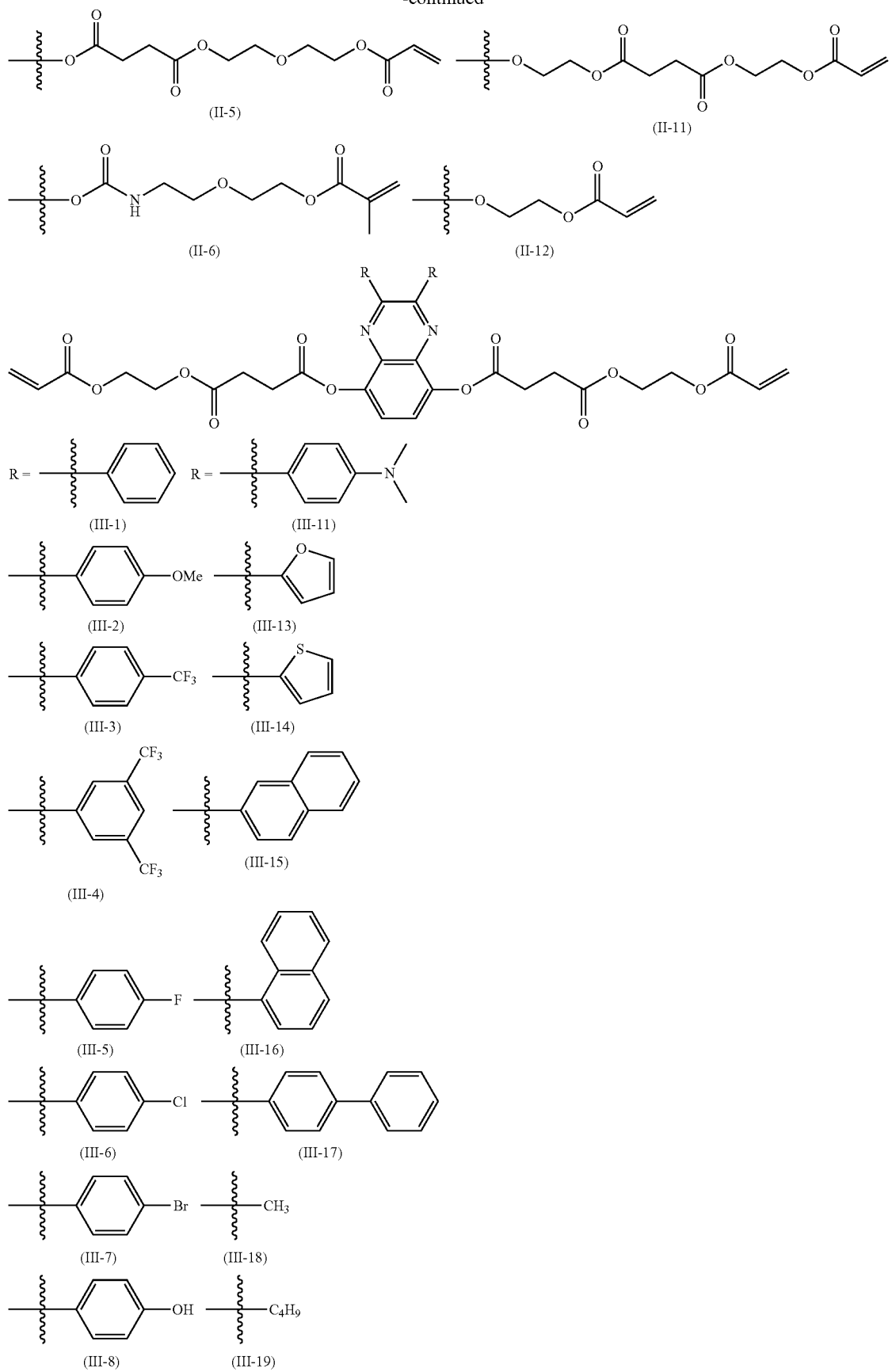

-continued
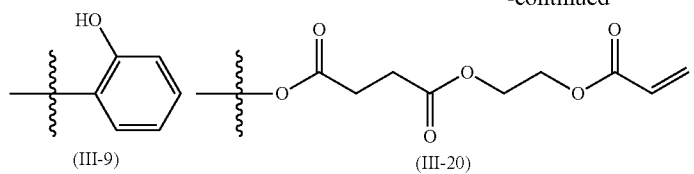
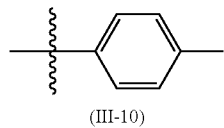
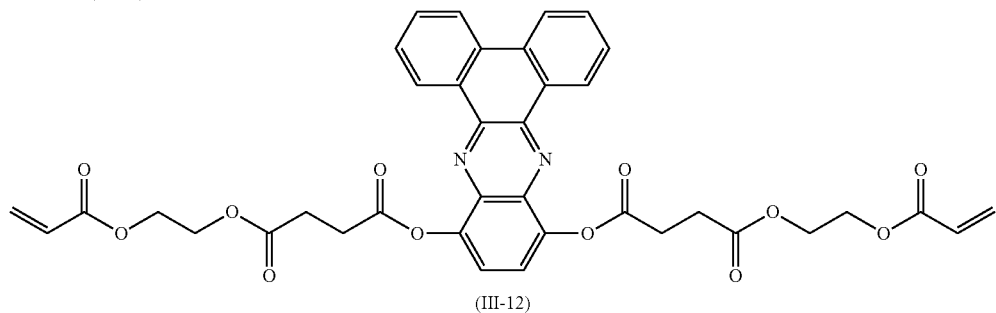
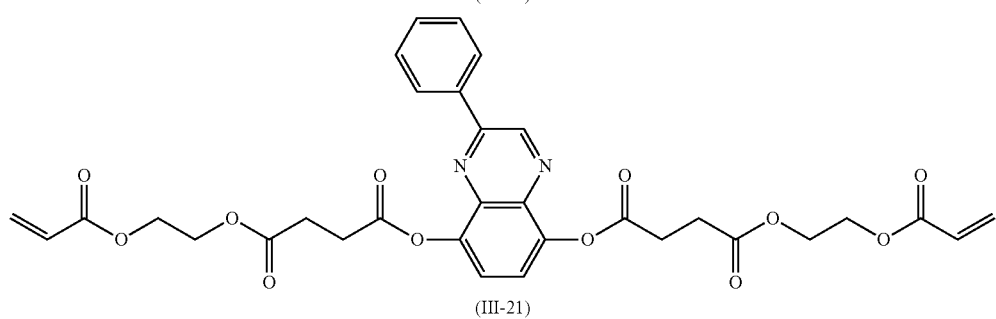
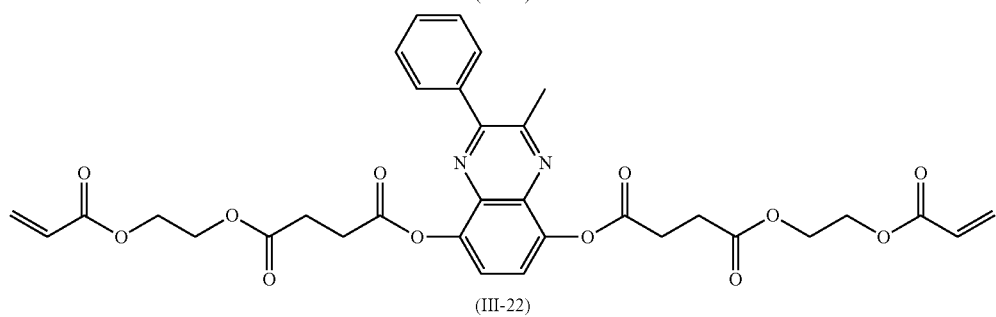
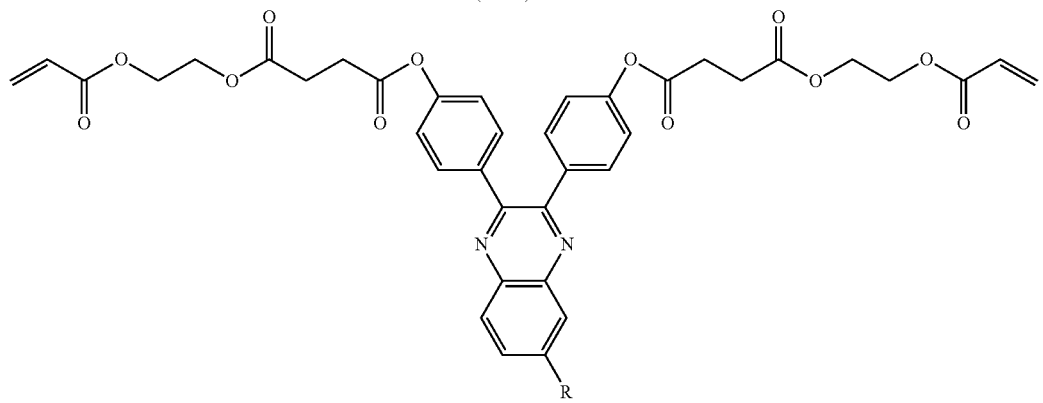

-continued
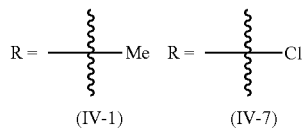
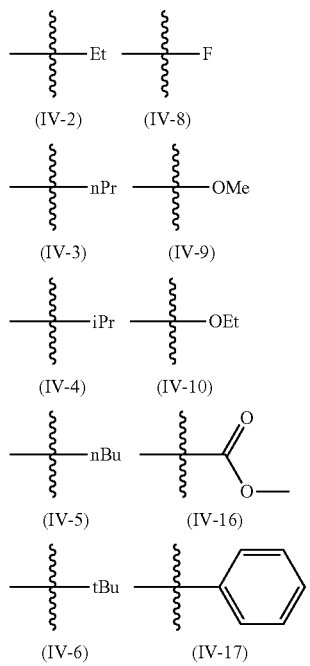
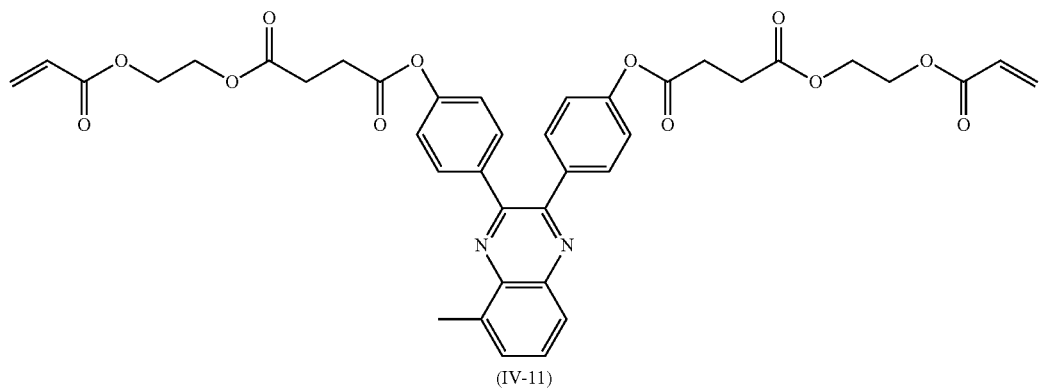
(IV-11)
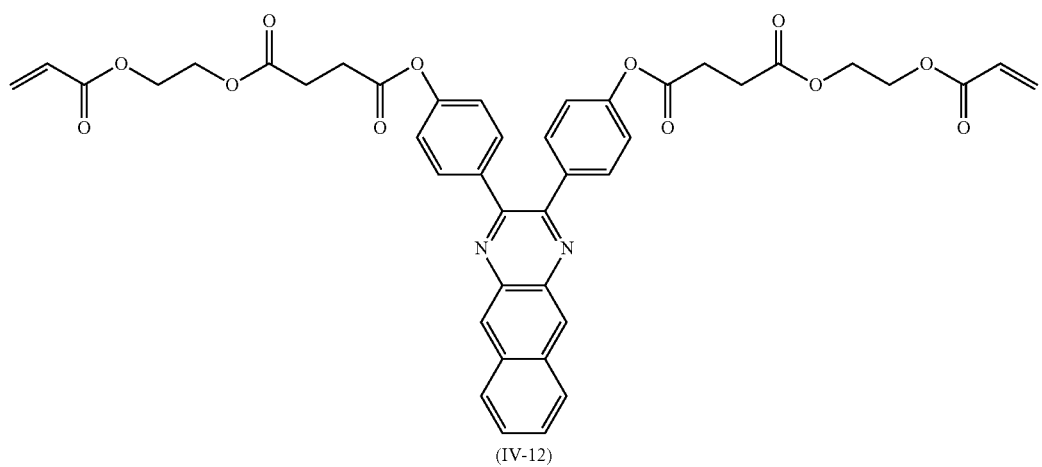
(IV-12)

-continued
(IV-13)
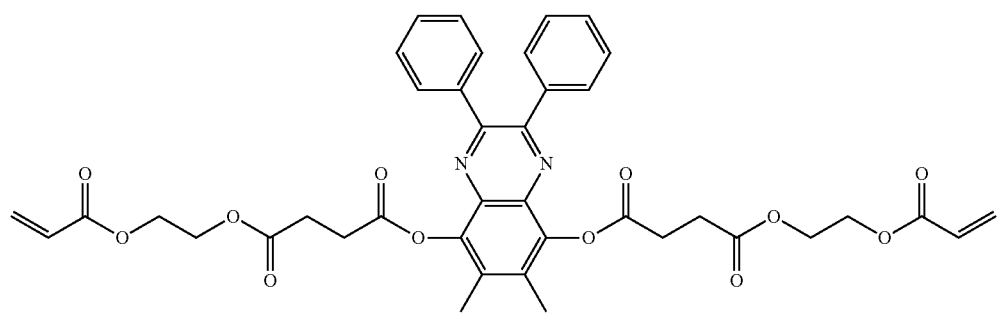
(IV-14)
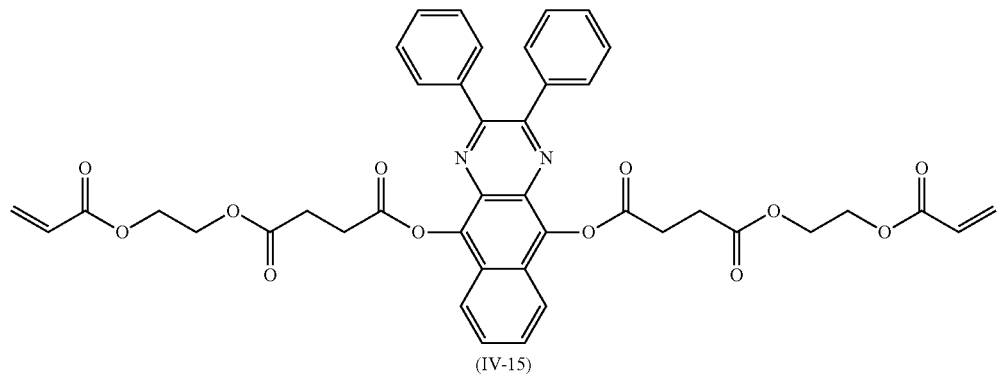
(IV-15)
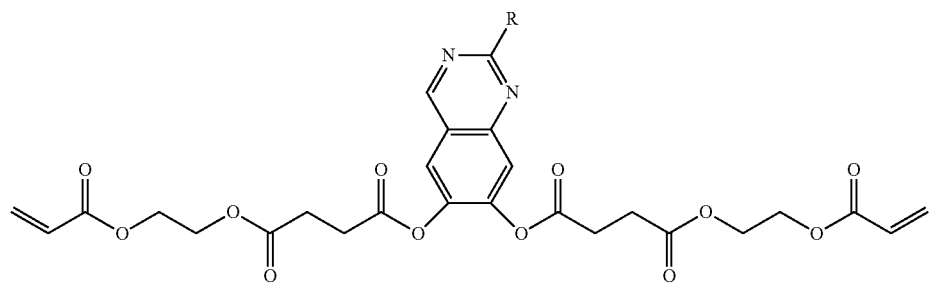
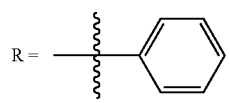
(V-1)
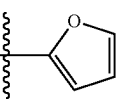
(V-8)
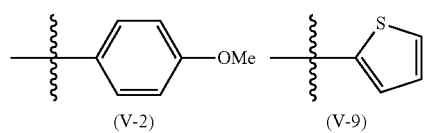
(V-2)
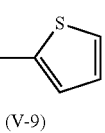
(V-9)

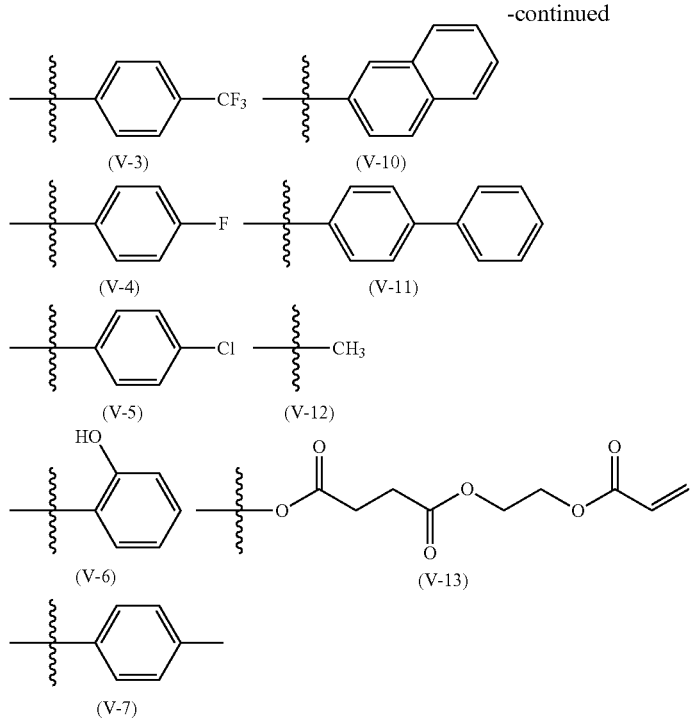

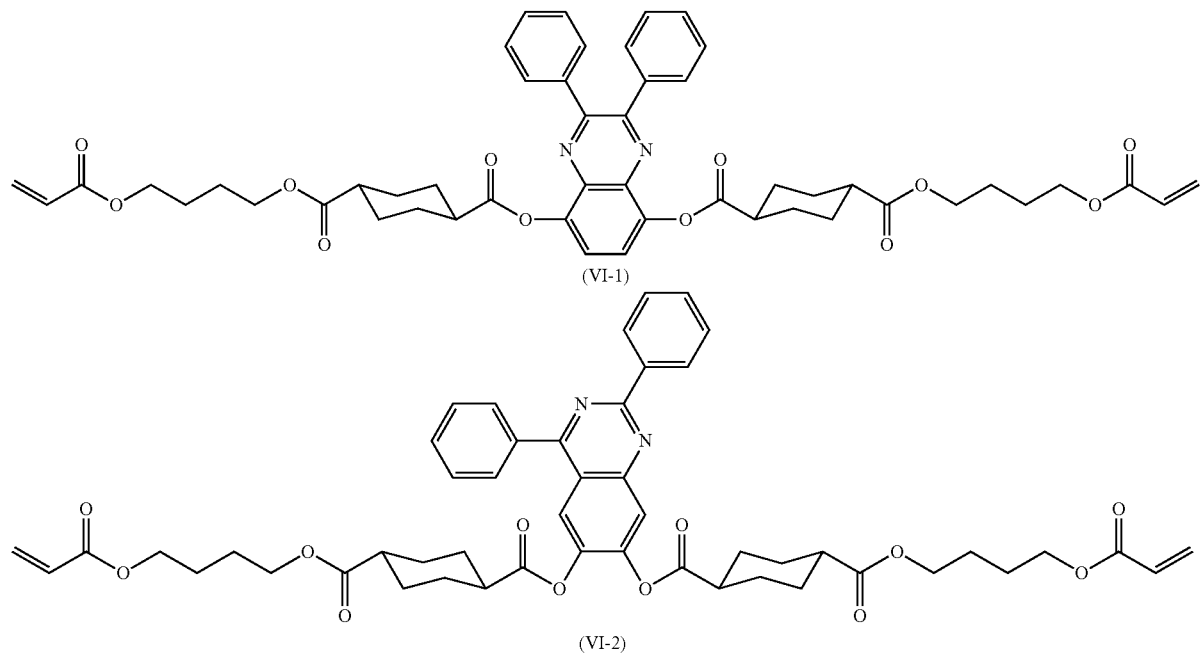

The compound represented by General Formula 1 has one or two or more asymmetric carbons in some cases, and regarding stereochemistry of such asymmetric carbons, compounds represented by General Formula 1 each independently can be any of an (R) isomer or an (S) isomer. In addition, the compound represented by Formula (A) may be a mixture of stereoisomers such as optical isomers or diastereoisomers. In other words, the compound represented by Formula (A) may be any kind of stereoisomer, may be any mixture of stereoisomers, or may be a racemate.

The content of the compound represented by General Formula 1 in the curable composition is preferably 30% to 99% by mass, is more preferably 35% by mass to 98% by mass, and is even more preferably 40% to 96% by mass with respect to the total mass of the curable composition. In a case where the content of the compound represented by General Formula 1 is within the above-mentioned range, a partial dispersion ratio ($\theta g$, F) higher than a predicted partial dispersion ratio ($\theta g$, F) is easily achieved in a cured product having a predetermined Abbe number.

Two or more compounds represented by General Formula 1 may be contained in the curable composition. In a case where two or more compounds represented by General Formula 1 are contained, the total content thereof is preferably within the above range.

(Other Components)

The curable composition of the present invention may further contain other components in addition to the compound represented by General Formula 1. Specific examples of other components include at least one selected from (meth)acrylate monomers, photoradical polymerization initiators, and thermal radical polymerization initiators.

((Meth)Acrylate Monomer)

The curable composition may contain a (meth)acrylate monomer. The (meth)acrylate monomer may be a polyfunctional (meth)acrylate monomer having two or more (meth) acryloyl groups in a molecule, or may be a monofunctional (meth)acrylate monomer having one (meth)acryloyl group in a molecule.

Specific examples of (meth)acrylate monomers include a (meth)acrylate monomer described in paragraphs 0037 to 0046 of JP2012-107191A.

The (meth)acrylate monomer used in the present invention may be monofunctional or polyfunctional. Examples thereof include the following monomer 1 (phenoxyethyl acrylate), monomer 2 (benzyl acrylate), monomer 3 (tricyclodecane dimethanol diacrylate), or monomer 4 (dicyclopentanyl acrylate), and the like. A molecular weight of the (meth)acrylate monomer is preferably 100 to 500.

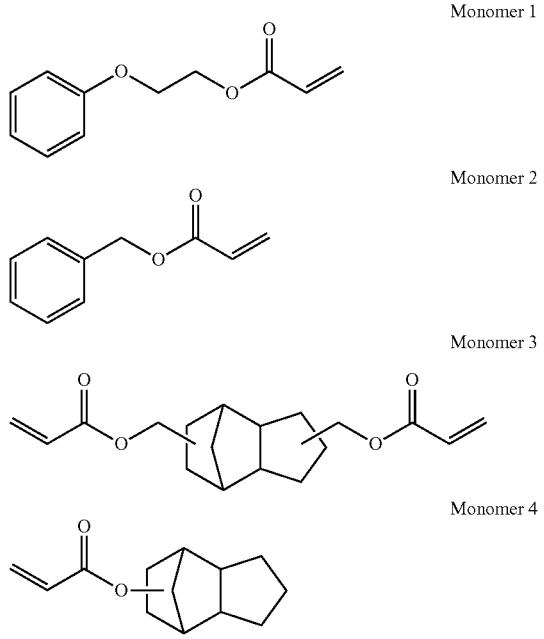

A method of obtaining the (meth)acrylate monomer is not particularly limited, and the compound may be commercially available or may be produced by synthesis. In a case of commercially obtaining the compound, for example, VISCOAT #192 PEA (Monomer 1) (manufactured by Osaka Organic Chemical Industry Ltd.), VISCOAT #160 BZA (Monomer 2) (manufactured by Osaka Organic Chemical Industry Ltd.), A-DCP (Monomer 3) (manufactured by Shin-Nakamura Chemical Co., Ltd.), or FA-513AS (Monomer 4) (manufactured by Hitachi Chemical Co., Ltd.) may be preferably used.

In a case where the curable composition of the present invention contains a (meth)acrylate monomer, the content of the (meth)acrylate monomer is preferably 1% to 80% by mass, more preferably 2% to 50% by mass, and even more preferably 3% to 40% by mass, with respect to the total mass of the curable composition. By adjusting an amount of (meth)acrylate monomer in the curable composition, a function of a cured product to relieve stress at the time of heat change can be adjusted.

<Polymer Having Radically Polymerizable Group in Side Chain>

The curable composition containing the compound represented by General Formula 1 may further contain a polymer having a radically polymerizable group in a side chain, in addition to the above-described compound. Because the polymer having a radically polymerizable group in a side chain functions to increase a viscosity of the curable composition, it can also be called a thickener or a thickening polymer. The polymer having a radically polymerizable group in a side chain can be added for adjusting a viscosity of the curable composition.

The polymer having a radically polymerizable group in the side chain may be a homopolymer or a copolymer. Among them, it is preferable that the polymer which has a radically polymerizable group in a side chain be a copolymer. In a case where the polymer having a radically polymerizable group in the side chain is a copolymer, it is sufficient that at least one copolymer component has a radically polymerizable group. In addition, in a case where the polymer having a radically polymerizable group in the side chain is a copolymer, the thickening polymer is more preferably a copolymer containing a monomer unit having a radically polymerizable group in the side chain and a monomer unit having an aryl group in the side chain.

Examples of radically polymerizable groups include a (meth)acrylate group, a vinyl group, a styryl group, and an allyl group. The polymer having a radically polymerizable group in the side chain preferably contains 5% to 100% by mass, more preferably 10% to 90% by mass, and even more preferably 20% to 80% by mass of repeating units having a radically polymerizable group.

In the following, specific examples of the polymer having a radically polymerizable group in the side chain preferably used in the present invention are exemplified, but the polymer having a radically polymerizable group in the side chain is not limited to the following structure. Each of the specific examples shown below is a copolymer, and each copolymer includes two or three structural units illustrated adjacent thereto. For example, the specific example described at the top is an allyl methacrylate-benzyl methacrylate copolymer.

In the structural formulas below, Ra and Rb each independently represent hydrogen atom or a methyl group. Note that a plurality of Ra's in one polymer may be the same or different. n represents an integer of 0 to 10, preferably 0 to 2, and more preferably 0 or 1.

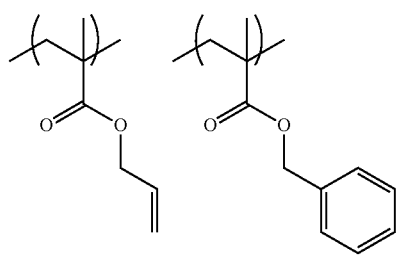

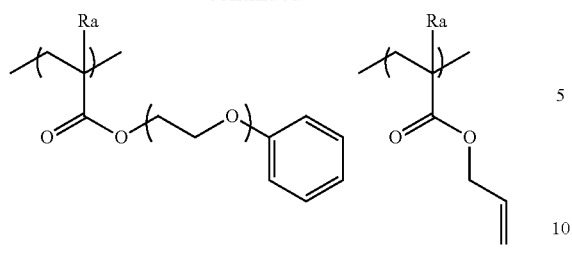
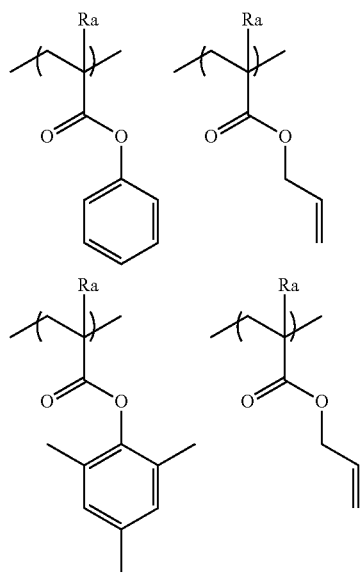
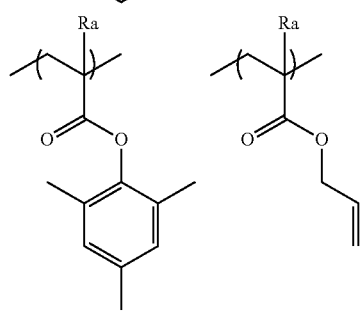
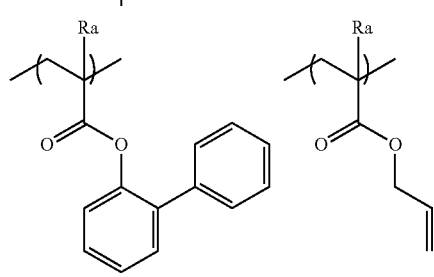
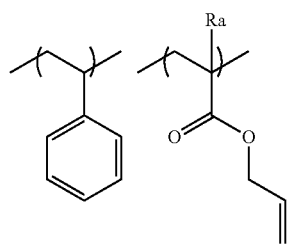
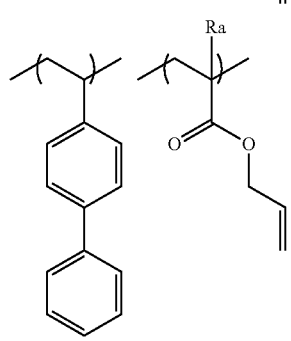
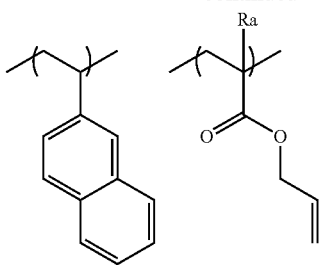
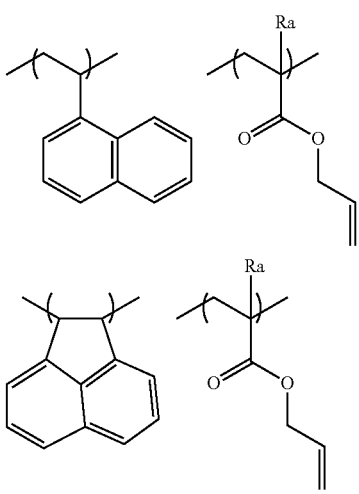
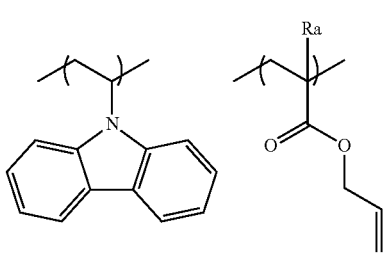
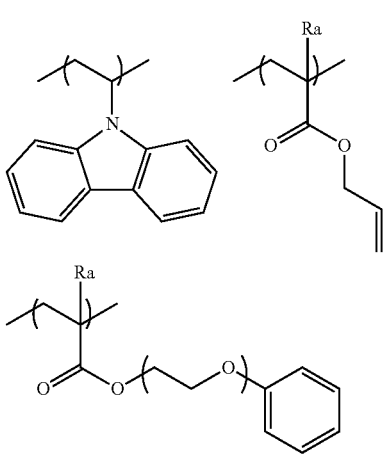
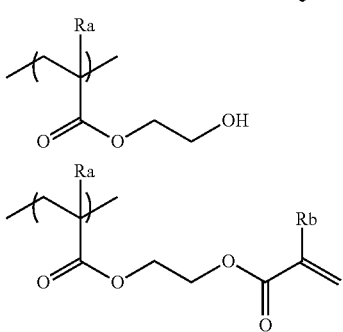

-continued
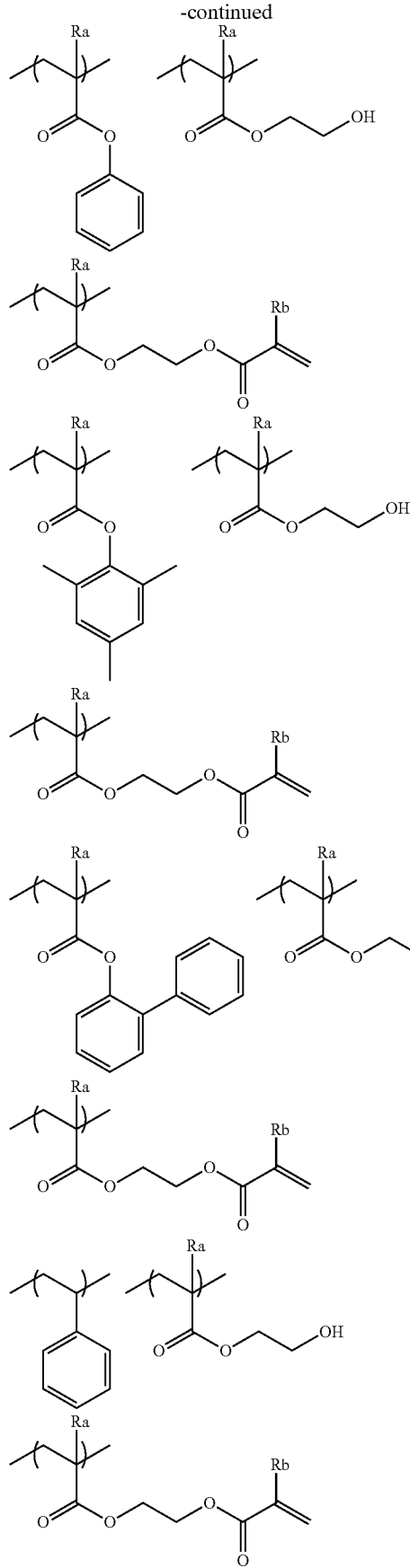
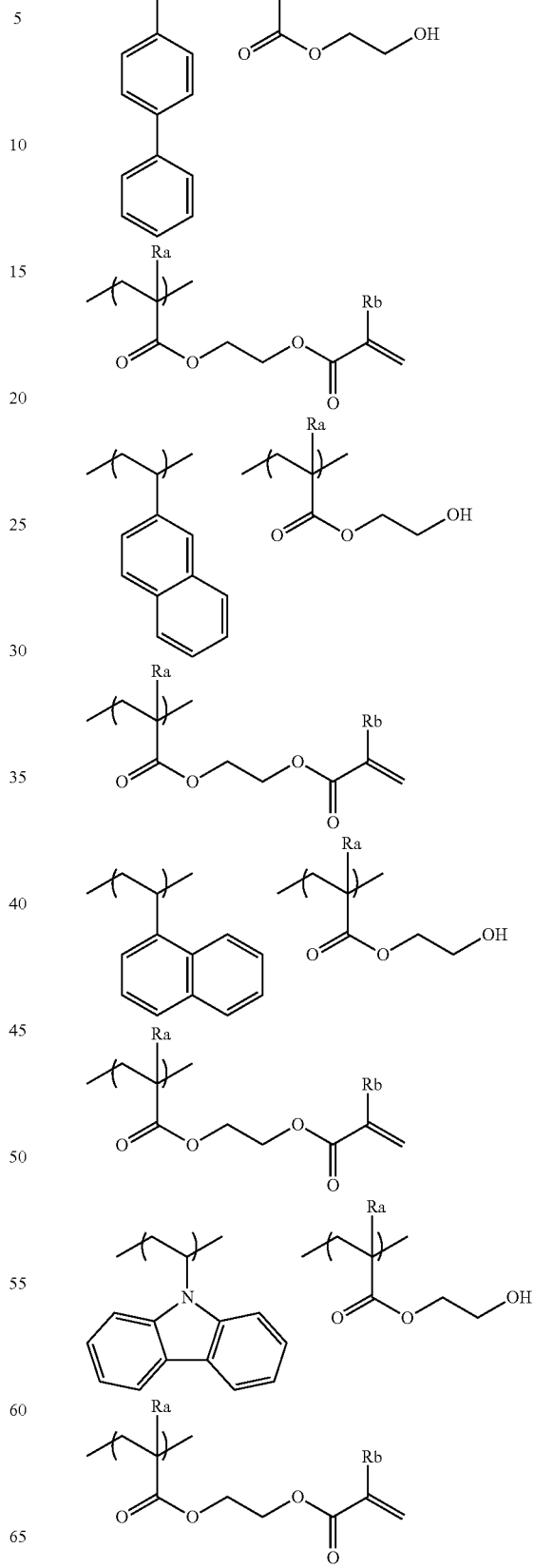

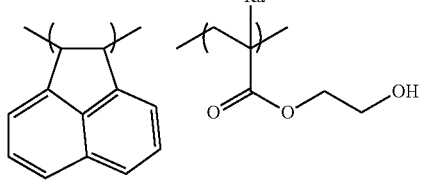
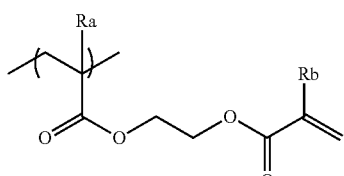
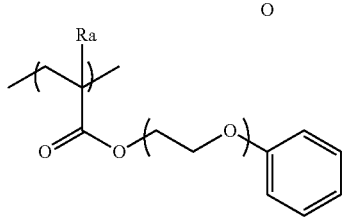
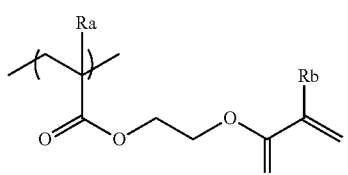
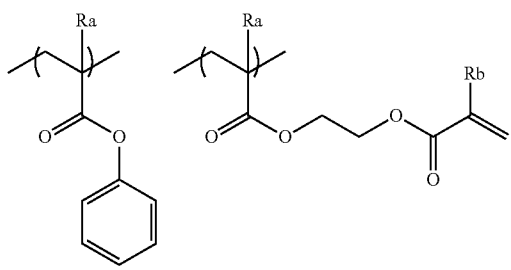
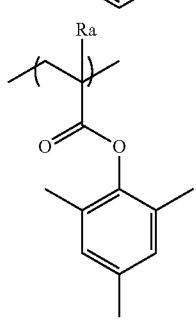
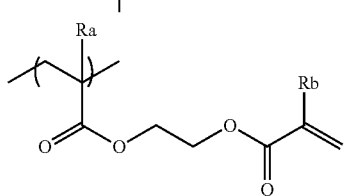
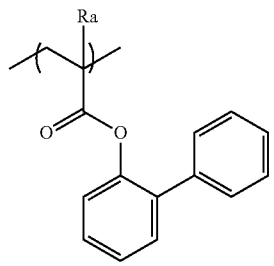
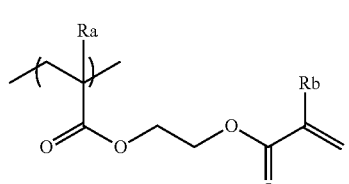
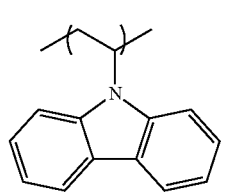
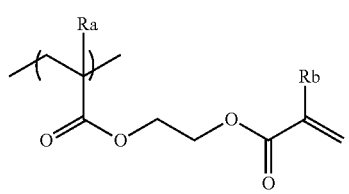
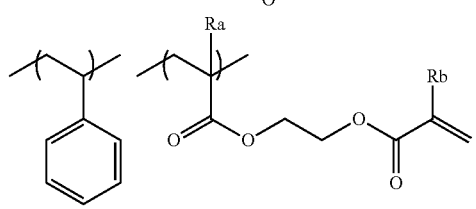
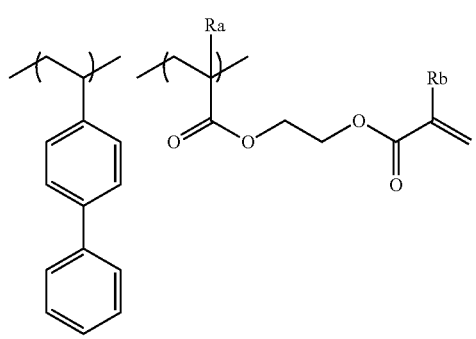

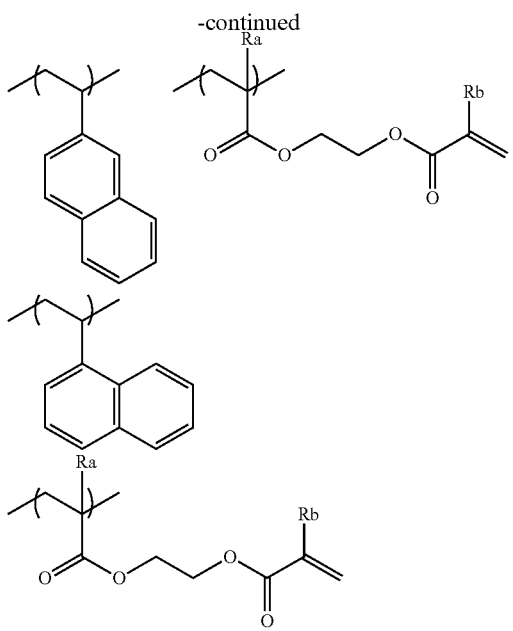

The molecular weight (weight-average molecular weight) of the polymer having a radically polymerizable group in the side chain is preferably 1,000 to 10,000,000, more preferably 5,000 to 300,000, and even more preferably 10,000 to 200,000. The glass transition temperature of the polymer having a radically polymerizable group in the side chain is preferably 50° C. to 400° C., more preferably 70° C. to 350° C., and even more preferably 100° C. to 300° C.

The content of the polymer having a radically polymerizable group in the side chain is preferably 40% by mass or less, more preferably 30% by mass or less, and even more preferably 25% by mass or less with respect to the total mass of the curable composition. The content of the polymer having a radically polymerizable group in the side chain may be 0% by mass, and an aspect in which a polymer having a radically polymerizable group in the side chain is not added is also preferable.

(Polymerization Initiator)

The curable composition containing the compound represented by General Formula 1 preferably contains at least one selected from a photoradical polymerization initiator or a thermal radical polymerization initiator.

<Thermal Radical Polymerization Initiator>

The curable composition preferably contains a thermal radical polymerization initiator. By this action, it is possible to mold a cured product having high heat resistance by thermally polymerizing the curable composition.

Specifically, the following compounds can be used as the thermal radical polymerization initiator. Examples of the thermal radical polymerization initiator include 1,1-di(t-hexylperoxy)cyclohexane, 1,1-di(t-butylperoxy)cyclohexane, 2,2-di(4,4-di-(t-butylperoxy)cyclohexyl)propane, t-hexylperoxyisopropyl monocarbonate, t-butylperoxy-3,5,5-trimethylhexanoate, t-butylperoxy laurate, dicumyl peroxide, di-t-butyl peroxide, t-butylperoxy-2-ethylhexanoate, t-hexylperoxy-2-ethylhexanoate, cumene hydroperoxide, t-butyl hydroperoxide, t-butylperoxy-2-ethylhexyl, 2,3-dimethyl-2,3-diphenylbutane, and the like.

The content of the thermal radical polymerization initiator is preferably 0.01% to 10% by mass, more preferably 0.05% to 5% by mass, and even more preferably 0.05% to 2% by mass, with respect to the total mass of the curable composition.

<Photoradical Polymerization Initiator>

The curable composition preferably contains a photoradical polymerization initiator. Specifically, the following compounds can be used as the photoradical polymerization initiator. Examples of the photoradical polymerization initiator include bis(2,6-dimethoxybenzoyl)-2,4,4-trimethylpentylphosphine oxide, bis(2,6-dimethylbenzoyl)-2,4,4-trimethylpentylphosphine oxide, bis(2,4,6-trimethylbenzoyl)-2,4,4-trimethylpentylphosphine oxide, bis(2,6-dichlorobenzoyl)-2,4,4-trimethylpentylphosphine oxide, 1-phenyl-2-hydroxy-2-methylpropan-1-one, 1-hydroxycyclohexyl phenyl ketone, 1-(4-isopropylphenyl)-2-hydroxy-2-methylpropan-1-one, 1,2-diphenylethanedione, methylphenyl glyoxylate, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)butanone-1,2,4,6-trimethylbenzoyl-diphenyl-phosphine oxide, and bis(2,4,6-trimethylbenzoyl)-phenylphosphine oxide.

Of the above, in the present invention, BASF's IRGACURE 184 (1-hydroxycyclohexyl phenyl ketone), IRGACURE 819 (bis(2,4,6-trimethylbenzoyl)-phenylphosphine oxide), IRGACURE 651 (2,2-dimethoxy-1,2-diphenylethane-1-one), 1-[4-(2-hydroxyethoxy)-phenyl]-2-hydroxy-2-methyl-1-propan-1-one, or 2-methyl-1-(4-methylthiophenyl)-2-morpholinopropan-1-one may be preferably used as the photoradical polymerization initiator.

The content of the photoradical polymerization initiator is preferably 0.01% to 5.0% by mass, more preferably 0.05% to 1.0% by mass, and even more preferably 0.05% to 0.5% by mass, with respect to the total mass of the curable composition.

The curable composition preferably contains both a photoradical polymerization initiator and a thermal radical polymerization initiator described above, and in this case, the total content of a photoradical polymerization initiator and a thermal radical polymerization initiator is preferably 0.01% to 5% by mass, more preferably 0.05% to 1.0% by mass, and even more preferably 0.05% to 0.5% by mass, with respect to the total mass of the curable composition.

<Other Additives and the Like>

Unless contrary to the gist of the present invention, the curable composition containing the compound represented by General Formula 1 may contain additives such as a polymer, a monomer, a dispersant, a plasticizer, a thermal stabilizer, or a mold release agent other than the components described above.

A viscosity of the curable composition containing the compound represented by General Formula 1 is preferably 20,000 mPa·s or less, is more preferably 15,000 mPa·s or less, is even more preferably 13,000 mPa·s or less, and is particularly preferably 10,000 mPa·s or less. By setting the viscosity of the curable composition within the above range, it is possible to improve handleability in a case of molding a cured product, thereby forming a high-quality cured product. A viscosity of the curable composition is preferably 2,000 mPa·s or more, is more preferably 3,000 mPa·s or more, is even more preferably 4,000 mPa·s or more, and is particularly preferably 5,000 mPa·s or more.

(Method for Producing Cured Product)

A method for producing a cured product includes a step of photocuring the above-described curable composition and/ or a step of thermosetting. Among them, a method for producing a cured product preferably includes a step of forming a semi-cured product by irradiating the curable composition with light or heating the curable composition; and a step of forming a cured product by irradiating the obtained semi-cured product with light or heating the obtained semi-cured product.

<Step of Forming Semi-Cured Product>

A step of forming a semi-cured product preferably includes a transfer step. A transfer step is a step of pressing a mold against the curable composition mentioned above. In the transfer step, the other mold is pressed against the curable composition injected into one of the pair of molds to spread the curable composition.

It is preferable that the mold used with the manufacturing method of cured products is a mold subjected to a chromium nitride treatment. Thereby, a favorable mold releasability can be obtained in a release step to be performed the subsequent steps, and the manufacture efficiency of the optical member can be increased.

Examples of chromium nitride treatment include a method of forming a chromium nitride film on the mold surface. Examples of methods for forming a chromium nitride film on the mold surface include a Chemical Vapor Deposition (CVD) method and a Physical Vapor Deposition (PVD) method. The CVD method is a method of forming a chromium nitride film on a substrate surface by reacting a source gas containing chromium and a source gas containing nitrogen at a high temperature. The PVD method is a method of forming a chromium nitride film on the surface of the substrate using an arc discharge (arc type vacuum deposition method). In this arc type vacuum deposition method, a cathode (evaporation source) made of chromium, for example, is placed in the vacuum vessel, an arc discharge is caused between the cathode and the wall of the vacuum vessel via a trigger, ionization of the metal by arc plasma is performed at the same time as vaporizing the cathode, a negative voltage is applied to the substrate, and about several tens of mTorr (1.33 Pa) of a reaction gas (for example, a nitrogen gas) is put into the vacuum vessel, and thereby the ionized metal and the reaction gas are reacted on the surface of the substrate to form a compound film. In the present invention, the chromium nitride treatment on the mold surface is performed by the CVD method or the PVD method.

In general, the mold can be heated while pressing the contents by combining two molds. In a case where a low-viscosity curable composition is injected into the mold, leakage into the mold clearance is caused. For this reason, it is preferable that the curable composition inject into a mold has a certain viscosity or more. In order to adjust the viscosity of the curable composition, a polymer having the above-described radically polymerizable group in the side chain may be added to the curable composition.

After the step of pressing the mold, a step of forming a semi-cured product is performed. The semi-cured product can be obtained by semi-curing the curable composition injected into the mold. In the step of forming the semi-cured product, photoirradiation or heating is performed. In the present specification, such a step can also be called a semi-curing step.

In the semi-curing step, the curable composition according to the present invention is subjected to at least one of light irradiation or heating. In semi-curing, there is generally no difference in Abbe number and partial dispersion ratio ($\theta$g, F) of a finally obtained cured product, regardless of whether light irradiation is performed or heating is performed. In the semi-curing step, it is preferable to form a semi-cured product having a complex viscosity of $10^5$ to $10^8$ mPa·s at 25° C. and a frequency of 10 Hz.

The term "semi-cured product" in the present specification refers to a product obtained by polymerizing a curable composition, which is not completely solid and has fluidity to some extent. A polymer of a curable composition in such a state that its complex viscosity at 25° C. and at a frequency of 10 Hz is $10^5$ to $10^8$ mPa·s is a semi-cured product. That is, those of which the upper limit value of the complex viscosity at 25° C. and at a frequency of 10 Hz is less than $1.0 \times 10^9$ mPa·s are considered to fall within a range of semi-cured products. On the other hand, the term "cured product" refers to a product produced by curing a curable composition by polymerization and is in a state of being completely solid.

The light used in the photoirradiation is preferably ultraviolet light or visible light and more preferably ultraviolet light. For example, a metal halide lamp, a low pressure mercury lamp, a high pressure mercury lamp, an ultrahigh pressure mercury lamp, a germicidal lamp, a xenon lamp, a light emitting diode (LED) light source lamp, or the like is suitably used. The atmosphere during photoirradiation is preferably air or an inert gas purged atmosphere and is more preferably an atmosphere purged with nitrogen until an oxygen concentration is 1% or less.

In a case of providing a heating and semi-curing step in the semi-curing step, the semi-curing by heating is carried out so that the complex viscosity of the semi-cured product at 25° C. and at a frequency of 10 Hz after heating is preferably $10^5$ to $10^8$ mPa·s.

The present invention may relate to a semi-cured product manufactured by the above-described method. Such a semi-cured product may be preferably used for a method for producing a cured product to be described later. The preferred range of the complex viscosity of the semi-cured product is the same as the preferred range of the complex viscosity of the semi-cured product in the above-described step of forming a semi-cured product.

The semi-cured product may not contain the photoradical polymerization initiator at all after the photoirradiation step, since the initiator is completely consumed in the step, or the photoradical polymerization initiator may remain in the semi-cured product.

In addition, the glass transition temperature of the semi-cured product is preferably −150° C. to 0° C., more preferably −50° C. to 0° C., and particularly preferably −20° C. to 0° C.

<Step of Forming Cured Product>

The step of forming a cured product preferably includes a thermal polymerization step of putting the semi-cured product in a molding mold for pressure deformation therein, and heating it therein for thermal polymerization to obtain a cured product or a photopolymerization step of photoirradiating the semi-cured product to obtain a cured product. In the present specification, such a step can also be called a curing step. The photoirradiation conditions and the heating conditions in the forming step of a cured product are the same as those in the semi-curing step described above.

In a case where the curing step is a thermal polymerization step, the molding mold used in the polymerization step is also referred to as a thermoforming mold. In general, the thermoforming mold is composed of two molding mold parts and is preferably designed so that contents can be heated under pressure in the combination of the two molding mold parts. In the method for producing a cured product, a metallic mold is more preferably used as the molding mold in the thermal polymerization step to obtain a cured product. The thermoforming mold of the type for use herein is described, for example, in JP2009-126011A. In addition, it is preferable that the mold is a mold subjected to a chromium nitride treatment.

In the thermal polymerization step, the semi-cured product put in a molding mold is deformed under pressure and heated for thermal polymerization to obtain a cured product. Pressure deforming and heating may be carried out simultaneously, or heating may be carried out after pressure deforming, or pressure deforming may be carried out after heating. Above all, pressure deforming and heating are preferably carried out at the same time. In addition, after pressure deforming and heating at the same time, it is preferable that the product further heated at a higher temperature after the pressure applied thereto has become stable.

In the thermal polymerization step, the semi-cured product is heated and cured at a temperature of 150° C. or higher to obtain a cured product.

The heating temperature is 150° C. or higher, preferably 160° C. to 270° C., more preferably 165° C. to 250° C., and even more preferably 170° C. to 230° C.

In this curing step, it is preferable to perform heating and pressure deformation. Thereby, the inverted shape of the inner surface of the mold can be accurately transferred to the cured product.

The pressure for the pressure deforming is preferably 0.098 MPa to 9.8 MPa, more preferably 0.294 MPa to 4.9 MPa, and particularly preferably 0.294 MPa to 2.94 MPa.

The time of thermal polymerization is preferably 30 to 1000 seconds, more preferably 30 to 500 seconds, and particularly preferably 60 to 300 seconds. The atmosphere during thermal polymerization is preferably air or an inert gas purged atmosphere and more preferably an atmosphere purged with nitrogen until an oxygen concentration is 1% or less.

A release step is provided after the curing step. In a case where thermal polymerization is performed in the curing step, it is preferable that the mold is separated from the cured product in a temperature range of 150° C. to 250° C. in the mold release step. By setting the temperature in the mold release step within the above range, the mold can be easily separated from the cured product, and the manufacture efficiency can be increased.

As mentioned above, although an example of the manufacturing method of the cured product of the embodiment of the present invention was described, the structure of the present invention is not restricted thereto, and it can be suitably changed within the range which does not deviate from the present invention. For example, the mold used in the transfer step and the semi-curing step may be used as it is in the curing step; or after performing the semi-curing step, the mold may be pulled away from the semi-cured product, and the semi-cured product may be moved to another mold (thermoforming mold) to perform the curing step. In this case, it is preferable that the above-described chromium treatment is performed on the mold used in the semi-curing step and the curing step.

Furthermore, in the semi-curing step, the curable composition in the mold may be irradiated with light and heated. Thereby, the semi-cured product which has a desired degree of curing can be obtained reliably.

(Semi-Cured Product)

The semi-cured product can be formed by semi-curing the above-described curable composition. The semi-cured product is preferably a semi-cured product produced by the above-mentioned method for producing a semi-cured product. In addition, the semi-cured product preferably has a complex viscosity of $10^5$ to $10^8$ mPa·s and a frequency of 10 Hz at 25° C.

The cured product of the embodiment of the present invention may be formed by curing the semi-cured product described above.

(Size)

The cured product of the embodiment of the present invention preferably has a maximum thickness of 0.1 to 10 mm. The maximum thickness is more preferably 0.1 to 5 mm, and particularly preferably 0.15 to 3 mm. The cured product according to the embodiment of the present invention is preferably a circular shape with the maximum diameter of 1 to 1,000 mm. The maximum diameter is more preferably 2 to 200 mm, and particularly preferably 2.5 to 100 mm.

(Optical Member)

The present invention also relates to an optical member including the above-described cured product. Since the cured product of the embodiment of the present invention is a molded object excellent in the optical characteristic, it is preferably used for an optical member. The type of the optical member of the embodiment of the present invention is not particularly limited. In particular, the cured product according to the embodiment of the present invention is suitably used for optical members that utilize the excellent optical properties of curable compositions, especially for light-transmissive optical members (so-called passive optical members). Examples of optically-functional devices including such optical members include various types of display devices (a liquid crystal display, a plasma display, and the like), various types of projector devices (an overhead projector (OHP), a liquid crystal projector, and the like), optical fiber communication devices (an optical waveguide, a light amplifier, and the like), and image-capturing devices such as a camera and a video.

Examples of the passive optical members for use in optically-functional devices include lenses, prisms, prism sheets, panels (plate-like molded bodies), films, optical waveguides (film-like optical waveguide, a fiber-like optical waveguide, and the like), optical discs, and LED sealants. If desired, the passive optical members may be provided with an optional coating layer, such as a protective layer for preventing mechanical damage of the coating surface by friction or abrasion, a light-absorbing layer for absorbing the light having an undesirable wavelength to cause degradation of inorganic particles, substrates and others, a blocking layer for suppressing or preventing permeation of reactive small molecules such as moisture or oxygen gas, an antiglare layer, an antireflection layer, a layer of low refractive index, or the like, as well as any additional functional layer. Specific examples of the optional coating layer include a transparent conductive film or a gas barrier film formed of an inorganic oxide coating layer, and a gas barrier film or hard coating film formed of an organic coating layer. The coating method for forming the coating layer may be any known coating method such as a vacuum deposition method, a CVD method, a sputtering method, a dip coating method, or a spin coating method.

APPLICATION EXAMPLES

The optical member obtained from the cured product according to the embodiment of the present invention is especially preferable for a lens substrate. The lens substrate manufactured using the curable composition of the present invention has a low Abbe number and preferably has high refractivity, light transmittance, and lightweight properties, and is excellent in optical properties. By suitably adjusting the type of monomer constituting the curable composition, it is possible to control the refractive index of the lens substrate in any desired manner.

In addition, in the present specification, the "lens substrate" refers to a single member capable of exhibiting a lens function. On and around the surface of the lens substrate, any film and member may be provided depending on the use environment and applications of lenses. For example, a protective film, an antireflection film, a hard coating film, or the like may be formed on the surface of the lens substrate. Further, it can be a compound lens in which a glass lens substrate or a plastic lens substrate is laminated. It is also possible to make the periphery of the lens substrate intrude and be fixed in a substrate holding frame. However, those films and frames are additional members to the lens substrate and therefore differ from the lens substrate itself referred to in the present specification.

In a case of using the lens substrate for lenses, the lens substrate itself may be used as a lens by itself, or additional films or frames or additional lens substrates may be added thereto for use as a lens, as mentioned above. The type and the shape of the lens formed of the lens substrate are not particularly limited.

The lens substrate is preferably used for, for example, lenses for imaging devices such as mobile phones or digital cameras; lenses for movie devices such as TV or video cameras; and lenses for in-vehicle devices or endoscope lenses.

EXAMPLES

Hereinafter, the features of the present invention will be more specifically described with reference to Examples and Comparative Examples. In the following Examples, the materials to be used, amounts and ratios thereof, the details of the treatment and the treatment procedures, and the like may be suitably modified or changed without departing from the scope of the present invention. Accordingly, the scope of the present invention should not be limitedly interpreted by the following specific Examples.

Synthesis Example 1

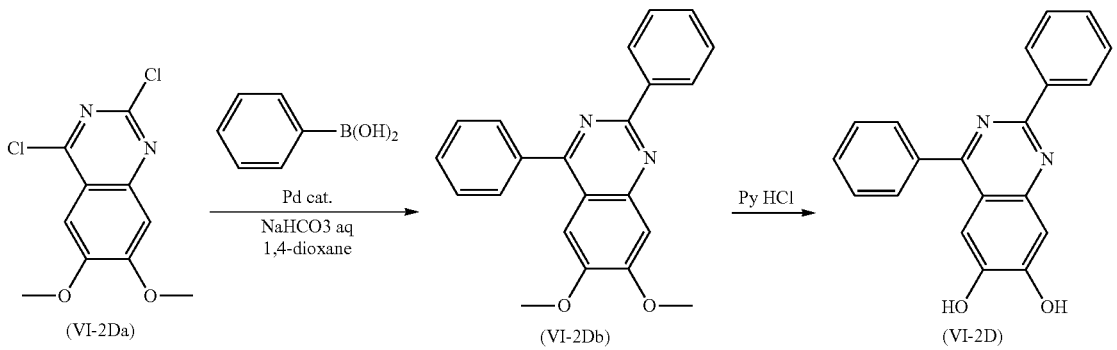

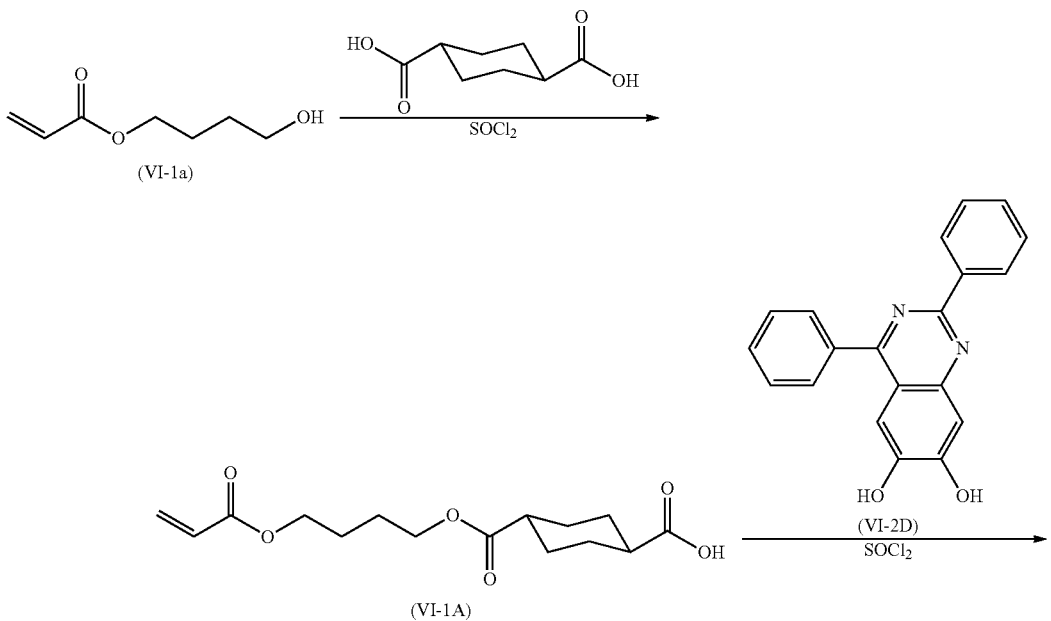

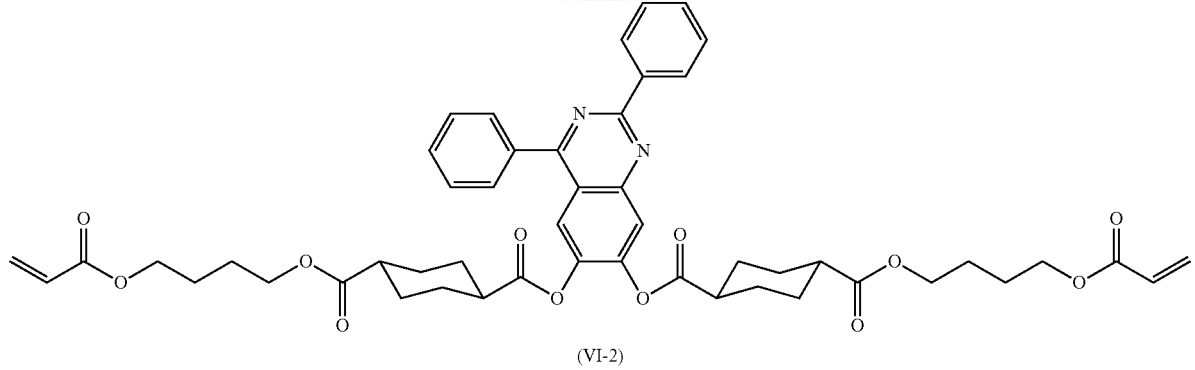

(VI-2)

<Synthesis of Compound (VI-2Db)>

5.0 g (19.3 mmol) of 2,4-dichloro-6,7-dimethoxyquinazoline (VI-2Da), 7.1 g (57.9 mmol) of phenylboronic acid, 1.1 g of dichlorobis[di-t-butyl(p-dimethylaminophenyl)phosphino]palladium (II), 100 mL of 1,4-dioxane, and 100 mL of a saturated aqueous solution of sodium hydrogen carbonate were mixed under a nitrogen atmosphere. After stirring the mixture at an internal temperature of 85° C. for 2 hours, the mixture was cooled to 25° C., ethyl acetate (300 mL) and water (200 mL) were added thereto, and the mixture was washed and separated. Thereafter, the mixture was concentrated and purified by column chromatography (yield 77%).

<Synthesis of Compound (VI-2D)>

After mixing 5.0 g of the compound (VI-2Db) and 50 g of pyridine hydrochloride, the mixture was stirred at 190° C. for 4 hours under a nitrogen atmosphere. Thereafter, 300 mL of water was added dropwise at 80° C. to precipitate a solid, and then the solid was cooled to 25° C. After the solid was filtered, it was washed with a water-methanol mixed solvent with a volume ratio of 3:1 (yield 95%).

<Synthesis of Compound (VI-1A)>

A compound (VI-1A) was synthesized according to a method described in paragraph 0113 of JP2016-053149A.

<Synthesis of Compound (VI-2)>

20.1 g (67.4 mmol) of the carboxylic acid compound (VI-1A), 185 mL of ethyl acetate, 46 mL of N,N-dimethylacetamide, and 60 mg of 2,6-di-t-butyl-4-methylphenol were mixed, and an internal temperature was cooled to 0° C. To the mixture, 7.75 g (65.1 mmol) of thionyl chloride was added dropwise at an internal temperature of 0° C. to 5° C. After stirring at 5° C. for 60 minutes, a solution of 8.7 g (27.6 mmol) of the compound (VI-2D) and 52 mL of THF was added dropwise at an internal temperature of 0° C. to 8° C.

Thereafter, 16.8 g of N,N-diisopropylethylamine was added dropwise at an internal temperature of 0° C. to 10° C. After stirring at an internal temperature of 20° C. to 25° C. for 1 hour, 40 mL of ethyl acetate, 165 mL of water, and 14 mL of concentrated hydrochloric acid were added and washed. The organic layer was washed with 140 mL of saturated saline and separated, and then washed with 100 mL of saturated saline and 10 mL of 7.5 wt % sodium bicarbonate water to be separated. Thereafter, concentration was performed to obtain an oily composition, which was then purified by column chromatography (yield 38%).

$^1$H-NMR (300 MHz, CDCl$_3$): δ (ppm) 1.40-1.60 (m, 8H), 1.60-1.80 (m, 8H), 2.00-2.20 (m, 8H), 2.20-2.40 (m, 4H), 4.15 (t, 4H), 4.24 (t, 4H), 5.84 (dd, 2H), 6.05-6.15 (m, 2H), 6.40 (dd, 2H), 7.35 (s, 2H), 7.45-7.55 (m, 6H), 7.60-7.70 (m, 4H).

Synthesis Example 2

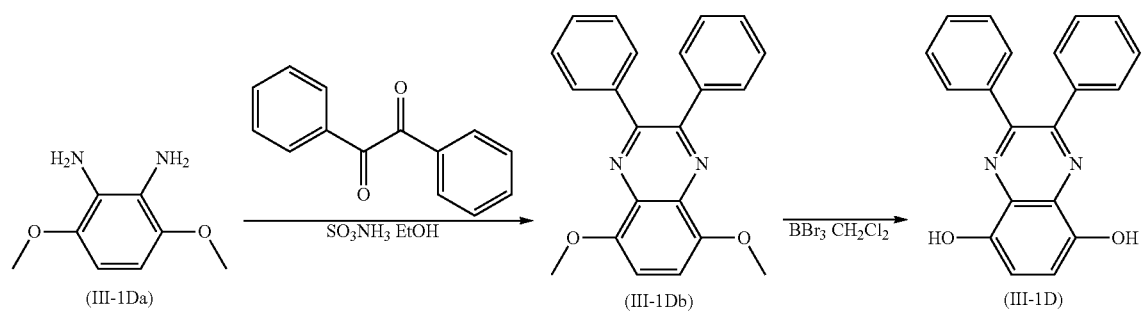

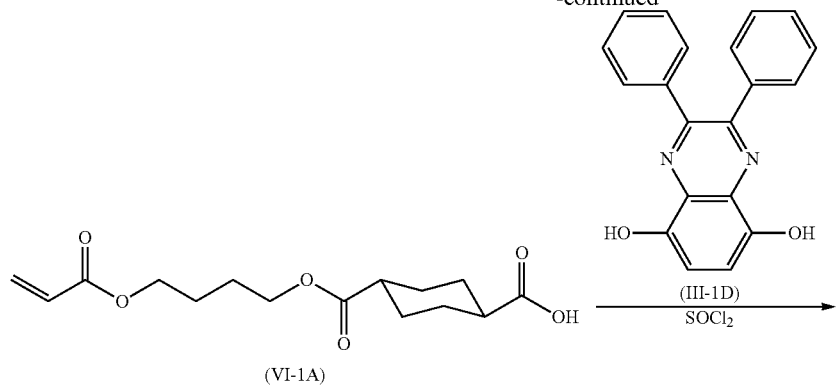

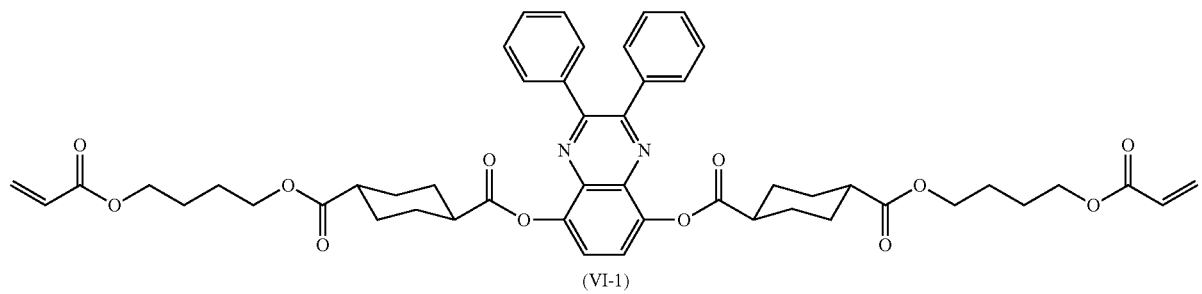

<Synthesis of Compound (III-1D)>

A compound (III-1D) was synthesized by the same method as in the synthesis of a compound (ex-2) described in Example 1 of JP2017-125009A, except that phenylglyoxal was changed to benzyl (yield 35%).

<Synthesis of Compound (VI-1)>

A compound (VI-1) (yield 85%) was obtained by the same method as in Synthesis Example 1, except that the compound (VI-2D) in the synthesis method of the compound (VI-2) described in Synthesis Example 1 was changed to the compound (III-1D).

$^1$H-NMR (300 MHz, CDCl$_3$) δ (ppm): 1.40-1.60 (m, 8H), 1.60-1.80 (m, 8H), 2.00-2.20 (m, 8H), 2.20-2.40 (m, 4H), 4.15 (t, 4H), 4.24 (t, 4H), 5.84 (dd, 2H), 6.05-6.15 (m, 2H), 6.40 (dd, 2H), 7.35 (s, 2H), 7.45-7.55 (m, 6H), 7.60-7.70 (m, 4H)

Synthesis Example 3

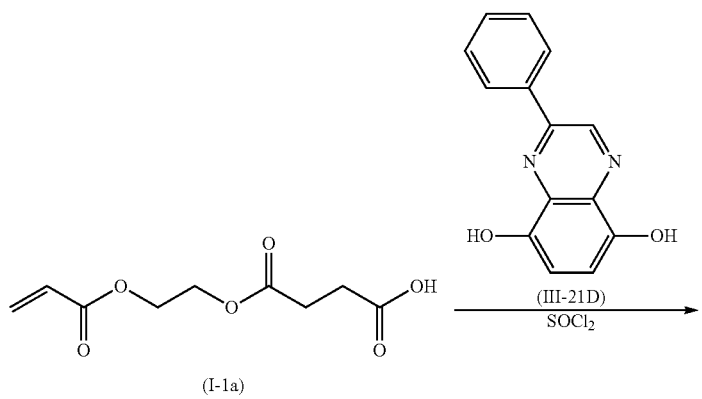

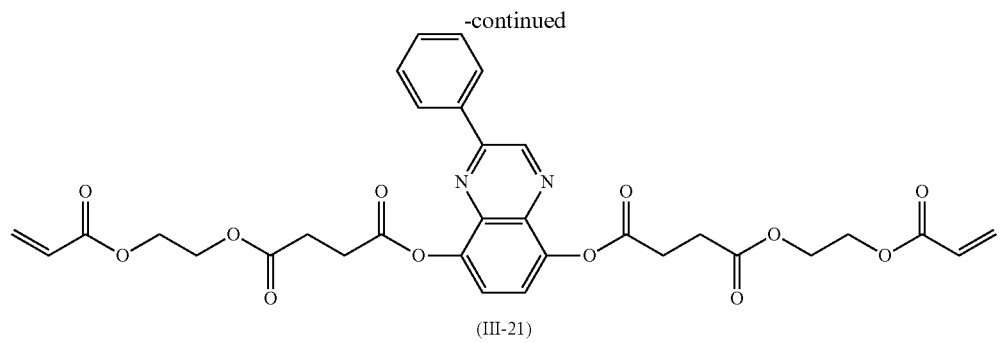

(III-21)

<Synthesis of Compound (III-21D)>

A compound (III-21D) was synthesized according to the method for the compound (ex-2) described in Example 1 of JP2017-125009A (yield 40%).

<Synthesis of Compound (III-21)>

7.3 g (33.7 mmol) of the carboxylic acid compound (I-1A), 93 mL of ethyl acetate, 23 mL of N,N-dimethylacetamide, and 30 mg of 2,6-di-t-butyl-4-methylphenol were mixed, and an internal temperature was cooled to 0° C. To the mixture, 3.88 g (32.6 mmol) of thionyl chloride was added dropwise at an internal temperature of 0° C. to 5° C. After stirring at 5° C. for 60 minutes, a solution of 3.3 g (13.8 mmol) of the compound (III-21D) and 26 mL of THF was added dropwise at an internal temperature of 0° C. to 8° C.

Thereafter, 8.4 g of N,N-diisopropylethylamine was added dropwise at an internal temperature of 0° C. to 10° C. After stirring at an internal temperature of 20° C. to 25° C. for 1 hour, 20 mL of ethyl acetate, 82.5 mL of water, and 7 mL of concentrated hydrochloric acid were added and washed. The organic layer was washed with 70 mL of saturated saline and separated, and then washed with 50 mL of saturated saline and 5 mL of 7.5 wt % sodium bicarbonate water to be separated. Thereafter, concentration was performed to obtain an oily composition, which was then purified by column chromatography (yield 84%).

$^1$H-NMR (300 MHz, CDCl$_3$): δ (ppm) 2.80 (t, 4H), 2.90-3.00 (m, 4H), 4.30-4.40 (m, 8H), 5.85 (d, 2H), 6.05-6.15 (m, 2H), 6.43 (d, 2H), 7.40-7.50 (m, 2H), 7.50-7.60 (m, 3H), 8.07 (d, 2H), 9.30 (s, 1H)

Synthesis Example 4

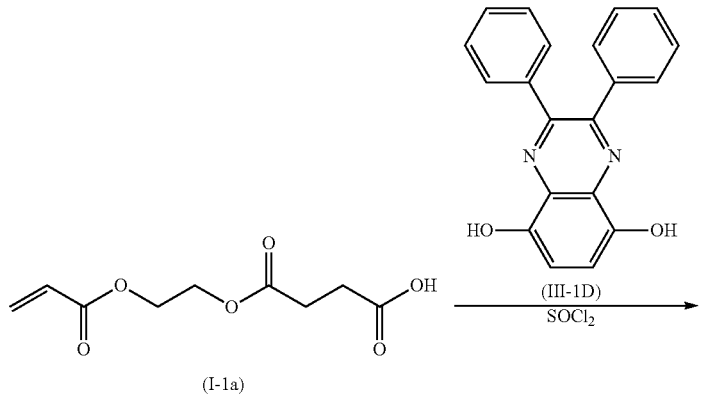

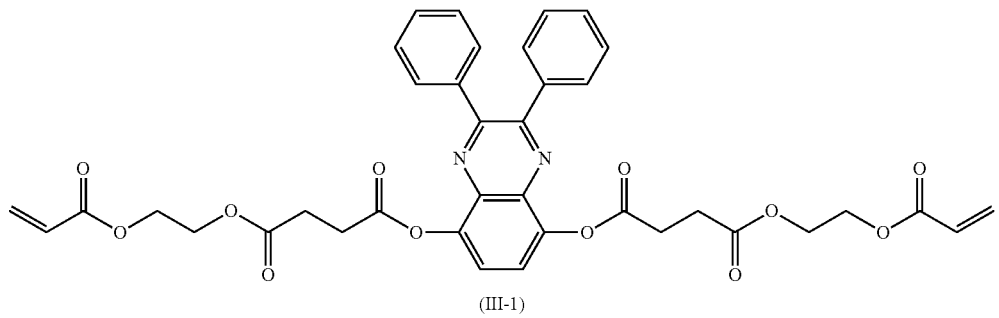

(III-1)

<Synthesis of Compound (III-1)>
A compound (III-1) (yield 81%) was obtained in the same manner as in Synthesis Example 3, except that the compound (I-21D) described in Synthesis Example 3 was changed to the compound (III-1D).
$^1$H-NMR (300 MHz, CDCl$_3$): δ (ppm) 2.80 (t, 4H), 2.95 (t, 4H), 4.30-4.40 (m, 8H), 5.85 (d, 2H), 6.05-6.15 (m, 2H), 6.43 (d, 2H), 7.35 (s, 2H), 7.45-7.60 (m, 6H), 7.60-7.70 (m, 4H)
Synthesis Example 5
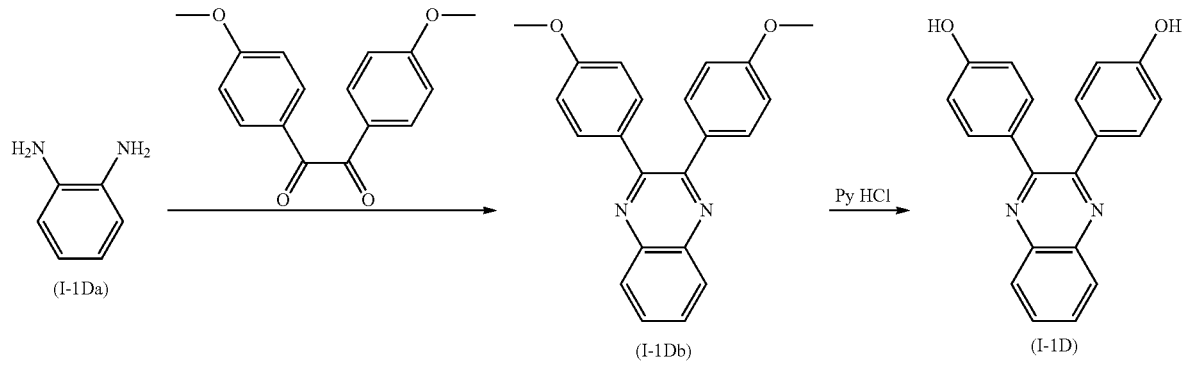
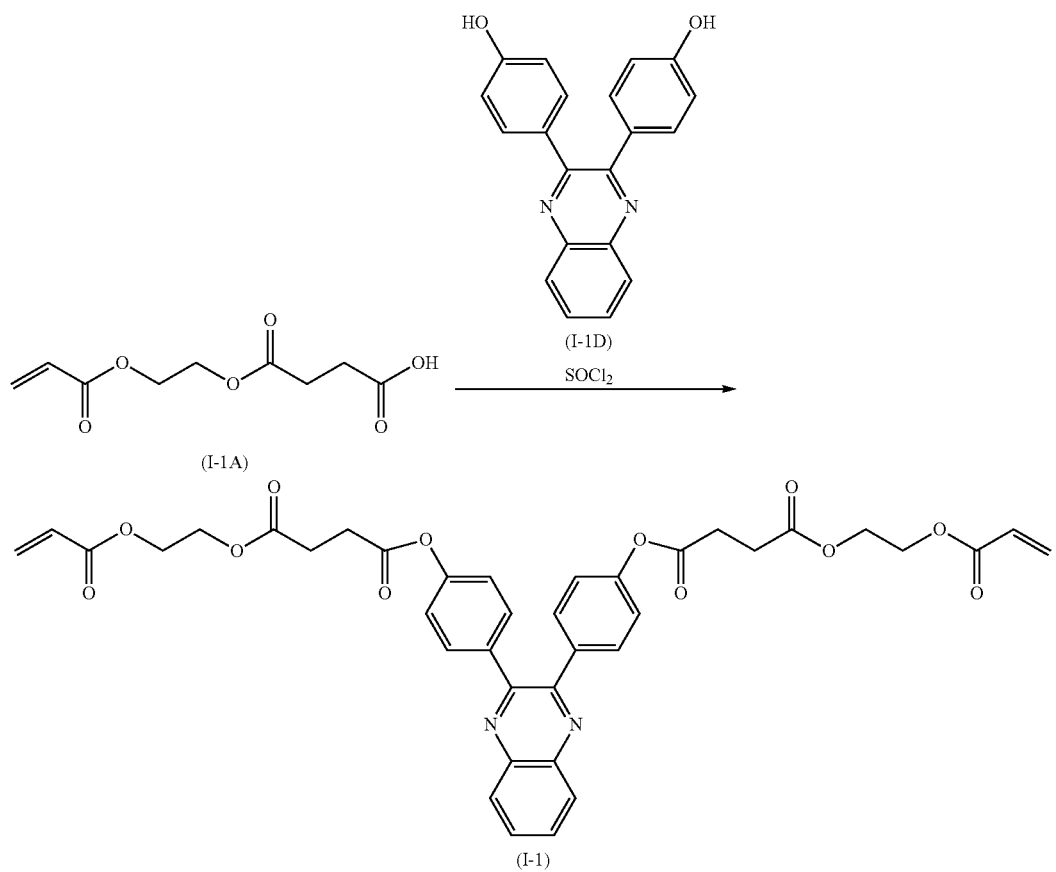

<Synthesis of Compound (I-1Db)>

After mixing 5.0 g (46.2 mmol) of 1,2-phenylenediamine (I-1Da), 12.5 g (46.2 mmol) of p-anisyl, and 80 mL of acetic acid, 125 mg of 2-iodoxybenzoic acid was added. After stirring the mixture at 25° C. for 2 hours, the precipitated compound (I-1Db) was filtered and washed with 50 mL of methanol (yield 65%).

<Synthesis of Compound (I-1D)>

A compound (I-1D) (yield 93%) was obtained by the same method except that the compound (VI-2Db) in the synthesis of the compound (VI-2D) of Synthesis Example 1 was changed to the compound (I-Db).

<Synthesis of Compound (I-1)>

A compound (I-1) (yield 75%) was obtained in the same manner as in Synthesis Example 3, except that the compound (III-21D) described in Synthesis Example 3 was changed to the compound (I-1D).

$^1$H-NMR (300 MHz, CDCl$_3$): δ (ppm) 2.80 (t, 4H), 2.92 (t, 4H), 4.30-4.40 (m, 8H), 5.85 (d, 2H), 6.05-6.15 (m, 2H), 6.43 (d, 2H), 7.10 (d, 4H), 7.70 (d, 4H), 7.70-7.80 (m, 2H), 8.10-8.20 (m, 2H)

Synthesis Example 6

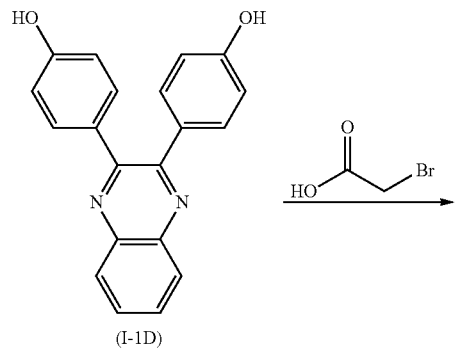

(I-1D)

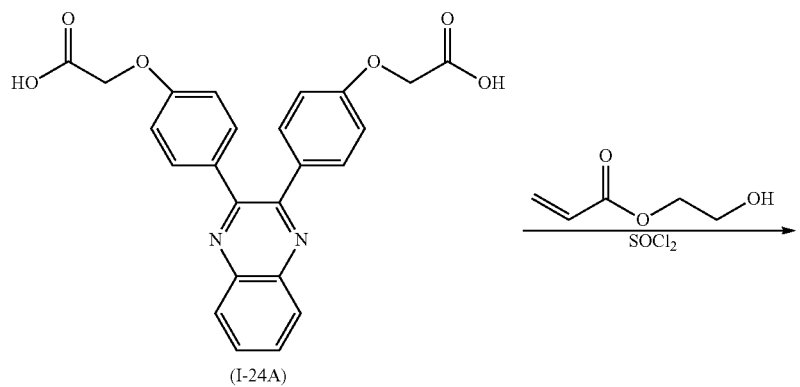

(I-24A)

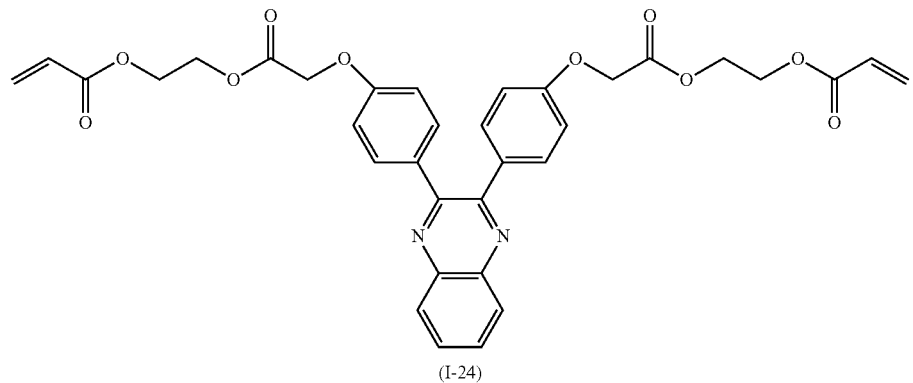

(I-24)

<Synthesis of Compound (I-24A)>

After mixing 10.1 g (32.2 mmol) of the compound (I-1D), 10.3 g (74.1 mmol) of bromoacetic acid, 1 g of tetrabutylammonium bromide, 260 mL of THF, and 200 mL of N,N-dimethylacetamide, 23.6 g of potassium carbonate was added thereto in small portions. Thereafter, an internal temperature was raised to 80° C., and the mixture was stirred for 10 hours. Thereafter, after cooling to 25° C., the solution was added to 700 mL of 1N hydrochloric acid water, and the precipitated solid was filtered. The obtained solid was purified by column chromatography (yield 35%).

<Synthesis of Compound (I-24)>

7.3 g (16.9 mmol) of the carboxylic acid compound (I-24A), 93 mL of ethyl acetate, 30 mL of N,N-dimethylacetamide, and 30 mg of 2,6-di-t-butyl-4-methylphenol were mixed, and an internal temperature was cooled to 0° C. To the mixture, 3.88 g (32.6 mmol) of thionyl chloride was added dropwise at an internal temperature of 0° C. to 5° C. After stirring at 5° C. for 60 minutes, a solution of 4.3 g (37.2 mmol) of 2-hydroxyethyl acrylate and 26 mL of THF was added dropwise at an internal temperature of 0° C. to 8° C.

Thereafter, 8.4 g of N,N-diisopropylethylamine was added dropwise at an internal temperature of 0° C. to 10° C. After stirring at an internal temperature of 20° C. to 25° C. for 1 hour, 20 mL of ethyl acetate, 82.5 mL of water, and 7 mL of concentrated hydrochloric acid were added and washed. The organic layer was washed with 70 mL of saturated saline and separated, and then washed with 50 mL of saturated saline and 5 mL of 7.5 wt % sodium bicarbonate water to be separated. Thereafter, concentration was performed to obtain an oily composition, which was then purified by column chromatography (yield 73%).

$^1$H-NMR (300 MHz, CDCl$_3$): δ (ppm) 4.30-4.40 (m, 8H), 4.70 (s, 4H), 5.85 (d, 2H), 6.05-6.15 (m, 2H), 6.43 (d, 2H), 6.90 (d, 4H), 7.50 (d, 4H), 7.70-7.80 (m, 2H), 8.10-8.20 (m, 2H).

Synthesis Example 7

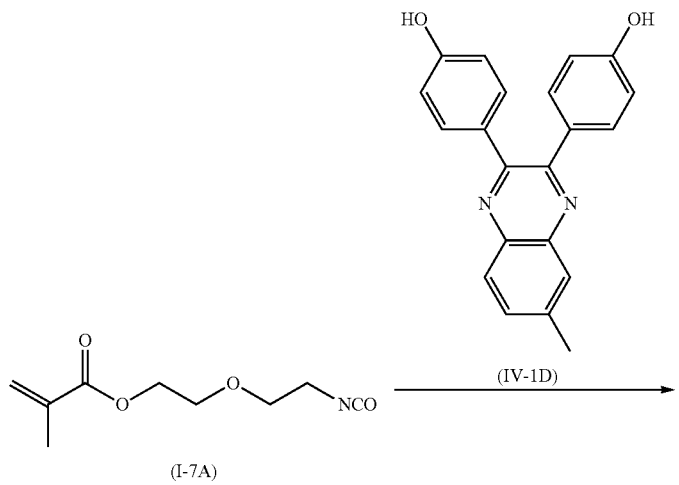

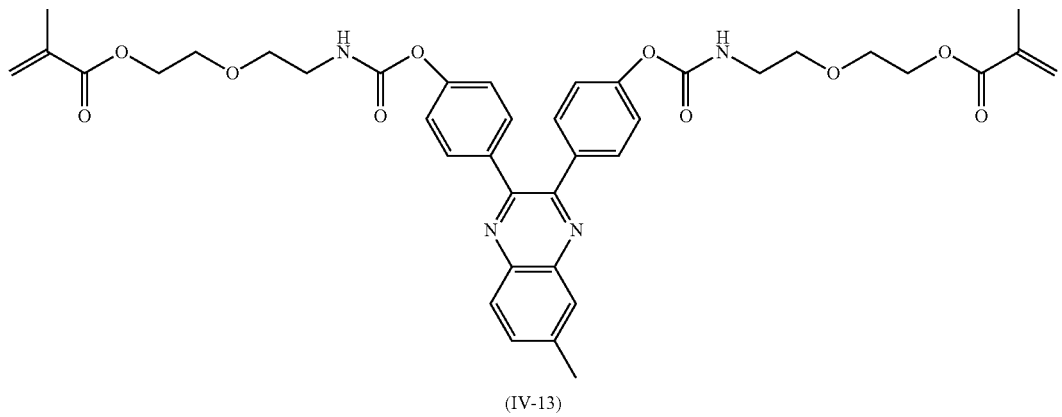

<Synthesis of Compound IV-1D>

A compound (IV-D) (yield 60%) was obtained by the same method as in Synthesis Example 5, except that 1,2-phenylenediamine in the synthesis method of the compound (I-1D) described in Synthesis Example 5 was changed to 3,4-toluenediamine.

<Synthesis of Compound IV-13>

4.4 g (22.0 mmol) of Karenz MOI-EG (1-7A, manufactured by Showa Denko K.K.), 3.6 g (10.9 mmol) of the compound (V-1D), 2 mL of N,N-dimethylacetamide, and 20 mL of chloroform were mixed, and the internal temperature was heated to 60° C. After stirring for 12 hours, the mixture was cooled to room temperature and further stirred for 12 hours. Next, after adding a saturated sodium bicarbonate water and stirring for 1 hour, liquid separation was performed. The collected organic layer was washed with 1 N hydrochloric acid and saturated brine, and then dried over anhydrous sodium sulfate, the solvent was removed with a rotary evaporator, and purification was performed by column chromatography (yield 78%).

$^1$H-NMR (400 MHz, CDCl$_3$): δ (ppm) 1.95 (s, 6H), 2.60 (s, 3H), 3.37 (m, 4H), 3.60-3.70 (m, 8H), 4.20 (t, 4H), 5.25 (br, s, 2H), 5.55 (s, 2H), 6.10 (s, 2H), 6.80-6.90 (m, 4H), 7.45-7.55 (m, 5H), 7.85-7.95 (m, 1H), 8.00-8.10 (m, 1H)

<Synthesis of Comparative Compound (Z-1)>

A compound having the following structure was synthesized by the method described in JP2014-043565A. This was designated as a comparative compound Z-1.

to 200° C. in an atmosphere having an oxygen concentration of 1% or less. Thereby, a thermally cured product was produced.

<Optical Characteristics Measurement>

An average value of "birefringence Δn" was calculated by measuring a birefringence within a circle of 10 mm in diameter including the center of the produced cured product using a birefringence evaluation apparatus (WPA-100, manufactured by Photonic Lattice, Inc.).

A "refractive index (nd)," an "Abbe number (vd)," and a "partial dispersion ratio (θg, F)" were measured by processing the cured product obtained by the cured sample production method (2) into a V-shaped block, and using a Kalnew precision refractometer KPR-2000 (manufactured by Shimadzu Device Corporation). The measurement was performed three times for each sample at 25° C. and an average value was taken as a measurement result.

A "refractive index (nd)" is a refractive index at a wavelength of 587.56 rm. In addition, an "Abbe number (vd)" and a "partial dispersion ratio (θg, F)" are values calculated from the refractive index measurement values at different wavelengths according to the following equations.

$$vd=(nd-1)/(nF-nC)$$

$$\theta g, F=(ng-nF)/(nF-nC)$$

Comparative compound Z-1

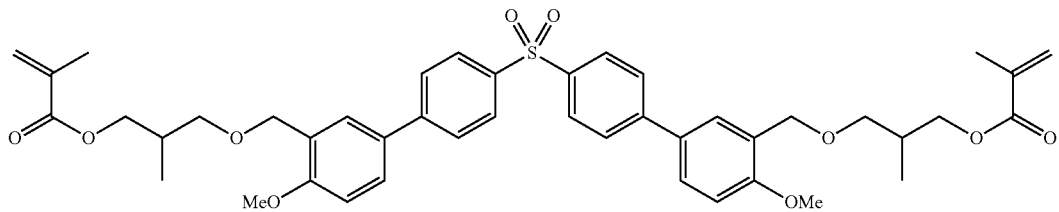

Examples 1 to 10 and Comparative Example 1

<Preparation of Curable Composition>

As shown in the following table, the compound represented by General Formula 1 or the comparative compound (a component (A)), a monomer B-1 (a (meth)acrylate monomer)(a component (B)), and a thermal polymerization initiator (t-butylperoxy-2-ethylhexanoate, product name: Perbutyl O (manufactured by NOF CORPORATION)) were mixed and stirred to be uniform. Thereby, a curable composition was prepared.

B-1

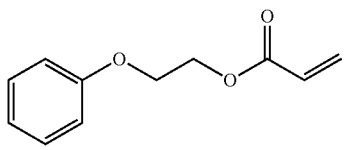

<Production of Cured Product Sample for Optical Property Measurement>

The prepared curable composition was poured into a transparent glass mold having a diameter of 20 mm so that a thickness of the cured product was 2 mm, and was heated Where nd represents a refractive index at a wavelength of 587.56 nm, nF represents a refractive index at a wavelength of 486.13 nm, nC represents a refractive index at a wavelength of 656.27 nm, and ng represents a refractive index at a wavelength of 435.83 nm.

The results are shown in Table 1.

<Evaluation of Moisture-Heat Resistance>

Each sample whose refractive index (nd) was measured was placed in a constant temperature and humidity chamber maintained at 90° C. and a relative humidity of 90%, stored for 24 hours, and then taken out. Next, after being allowed to stand at 25° C. and relative humidity 60% for 1 hour, a refractive index (nd) was measured, and an amount of change in the refractive index before and after the moisture-heat test was evaluated in the following three grades, A to C. The results are shown in Table 1.

A: A change in refractive index before and after the moisture-heat test was 0.0005 or less B: A change in refractive index before and after the moisture-heat test was more than 0.0005 and 0.001 or less C: A change in refractive index before and after the moisture-heat test was more than 0.001

TABLE 1

|  |  | Example 1 | Example 2 | Example 3 | Example 4 | Example 5 | Example 6 |
|---|---|---|---|---|---|---|---|
| Component (A) | VI-2 | 64.4 |  |  |  |  |  |
|  | VI-1 |  | 64.4 |  |  |  |  |
|  | III-21 |  |  | 64.4 |  |  |  |
|  | III-1 |  |  |  | 64.4 |  |  |
|  | I-1 |  |  |  |  | 64.4 |  |
|  | I-24 |  |  |  |  |  | 64.4 |
|  | IV-13 |  |  |  |  |  |  |
| Comparative compound | Z-1 |  |  |  |  |  |  |
| Component (B) | B-1 | 34.6 | 34.6 | 34.6 | 34.6 | 34.6 | 34.6 |
| Thermal polymerization initiator | Perbutyl O | 1 | 1 | 1 | 1 | 1 | 1 |
| Total |  | 100 | 100 | 100 | 100 | 100 | 100 |
| Characteristics of cured product | $\Delta n$ | 0.0005 | 0.0003 | 0.0004 | 0.0006 | 0.0002 | 0.0005 |
|  | nd | 1.515 | 1.520 | 1.518 | 1.532 | 1.531 | 1.533 |
|  | $\upsilon d$ | 27.5 | 25.5 | 25.8 | 25.2 | 24.8 | 22.1 |
|  | $\theta g, F$ | 0.72 | 0.74 | 0.74 | 0.76 | 0.76 | 0.79 |
|  | Moisture-heat resistance | B | A | A | A | A | A |

|  |  | Example 7 | Example 8 | Example 9 | Example 10 | Comparative Example 1 |
|---|---|---|---|---|---|---|
| Component (A) | VI-2 |  |  |  |  |  |
|  | VI-1 |  |  |  |  |  |
|  | III-21 |  |  |  |  |  |
|  | III-1 |  |  |  |  |  |
|  | I-1 |  |  |  |  |  |
|  | I-24 |  | 30 | 99 | 96 |  |
|  | IV-13 | 64.4 |  |  |  |  |
| Comparative compound | Z-1 |  |  |  |  | 64.4 |
| Component (B) | B-1 | 34.6 | 69 | 0 | 3 | 34.6 |
| Thermal polymerization initiator | Perbutyl O | 1 | 1 | 1 | 1 | 1 |
| Total |  | 100 | 100 | 100 | 100 | 100 |
| Characteristics of cured product | $\Delta n$ | 0.0009 | 0.0006 | 0.0008 | 0.0007 | 0.0005 |
|  | nd | 1.532 | 1.516 | 1.541 | 1.540 | 1.570 |
|  | $\upsilon d$ | 23.6 | 26.5 | 19.0 | 19.0 | 22.2 |
|  | $\theta g, F$ | 0.77 | 0.71 | 0.81 | 0.80 | 0.69 |
|  | Moisture-heat resistance | A | A | A | A | C |

In the table, an amount of each component is indicated by % by mass.

Based on the results shown in Table 1, it was found that a larger partial dispersion ratio ($\theta g, F$) was obtained in the examples of the present invention as compared to Comparative Example 1.

<Appearance Test>

With respect to Examples 6 and 8 to 10 in which only blending amounts of the component A and the component B were different, a cured product was separately produced, and an appearance test was performed.

The prepared curable composition was poured into a transparent glass mold having a diameter of 15 mm so that a thickness of the cured product was 2 mm, and was heated to 200° C. in an atmosphere having an oxygen concentration of 1% or less. Thereby, thermally cured products were produced.

The produced cured products were observed with a digital microscope manufactured by KEYENCE CORPORATION, and a product in which a change in shape such as distortion or crack was recognized was defined as a defective product, and a product in which such a change was not generated was defined as a non-defective product. As a result of evaluating 10 cured products, the number of non-defective products was 9 in Example 6, the number was 8 in Example 8, the number was 6 in Example 9, and the number was 8 in Example 10.

10. The compound according to claim 1 represented by any one of the following formulae:
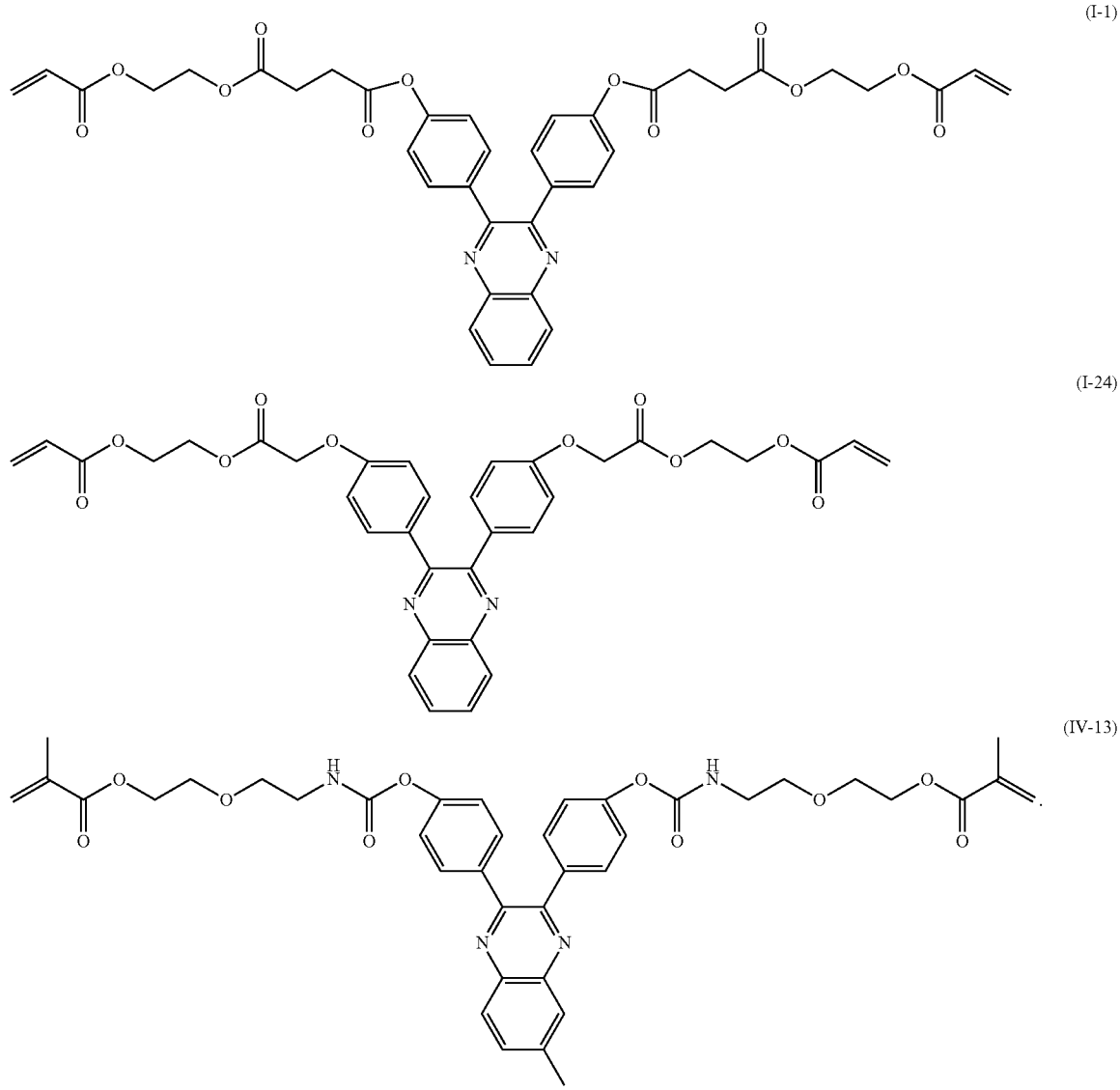

What is claimed is:

1. A compound represented by Formula 1:

$$\text{Pol}_1\text{-Sp}_1\text{-L}_1\text{-Ar-L}_2\text{-Sp}_2\text{-P}_2 \quad \text{(Formula 1)}$$

in the formula, Ar represents any group represented by Formulas 2-1 to 2-5,

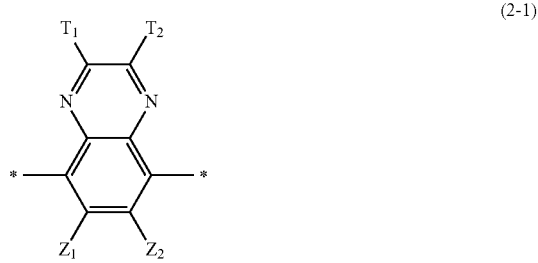

-continued (2-2)
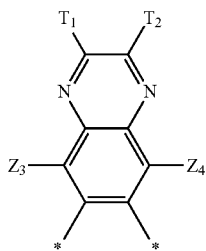

(2-3)
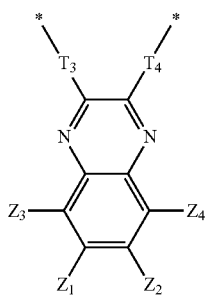

(2-4)
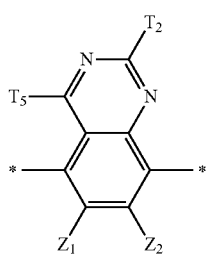

(2-5)
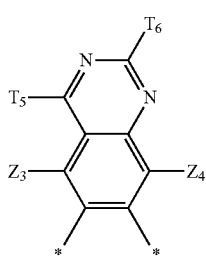

in Formulas 2-1 to 2-5, $Z_1$, $Z_2$, $Z_3$, and $Z_4$ each independently represents a hydrogen atom, an aliphatic hydrocarbon group which has 1 to 20 carbon atoms and may have a substituent, an alkoxy group which has 1 to 20 carbon atoms and may have a substituent, an alkoxycarbonyl group which has 1 to 20 carbon atoms and may have a substituent, an alicyclic hydrocarbon group which has 3 to 20 carbon atoms and may have a substituent, an aromatic hydrocarbon group which has 6 to 20 carbon atoms and may have a substituent, a halogen atom, a cyano group, a nitro group, $-NR_{12}R_{13}$, $SR_{12}$, or an aromatic heterocyclic ring which may have a substituent, where $R_{12}$ and $R_{13}$ each independently represents a hydrogen atom, or an alkyl group which has 1 to 6 carbon atoms and may have a substituent, $T_1$, $T_2$, $T_5$, and $T_6$ each independently represents a halogen atom, a cyano group, a nitro group, $-L_6-Sp_6-Pol_6$, an alicyclic hydrocarbon group which has 3 to 20 carbon atoms and may have a substituent, an aromatic hydrocarbon group which has 6 to 20 carbon atoms and may have a substituent, an aromatic heterocyclic group which may have a substituent, $NR_{12}R_{13}$, or $SR_{12}$, $L_6$ is synonymous with $L_1$, $Sp_6$ represents a single bond, or a linking group selected from the group consisting of a linear alkylene group which has 1 to 30 carbon atoms and may have a substituent and a group in which one or two or more non-adjacent $-CH_2-$'s are substituted by $-O-$, $-S-$, $-C(=O)-$, $-OC(=O)-$, $-C(=O)O-$, $-OC(=O)O-$, $-NR_{201}C(=O)-$, $-C(=O)NR_{202}-$, $-OC(=O)NR_{203}-$, $-NR_{204}C(=O)O-$, $-SC(=O)-$, or $-C(=O)S-$ in the linear alkylene group which has 1 to 30 carbon atoms and may have a substituent, where $R_{201}$, $R_{202}$, $R_{203}$, and $R_{204}$ each independently represents $-Sp_4-Pol_4$ or a halogen atom, $Sp_4$ represents a single bond or a divalent linking group, $Pol_4$ and $Pol_6$ are each independently synonymous with $Pol_1$, and $T_3$ and $T_4$ each independently represents a divalent aromatic hydrocarbon group which has 6 to 12 carbon atoms and may have a substituent or a divalent aromatic heterocyclic group which may have a substituent, in Formula (1), $L_1$ and $L_2$ each independently represents a single bond, or a linking group selected from the group consisting of $-O-$, $-S-$, $-C(=O)-$, $-OC(=O)-$, $-C(=O)O-$, $-OC(=O)O-$, $-NR_{101}C(=O)-$, $-C(=O)NR_{102}-$, $-OC(=O)NR_{103}-$, $-NR_{104}C(=O)O-$, $-SC(=O)-$, and $-C(=O)S-$, where $R_{101}$, $R_{102}$, $R_{103}$, and $R_{104}$ each independently represents $-Sp_3-Pol_3$ or a halogen atom, $Sp_1$ and $Sp_2$ each independently represents a single bond, or a linking group selected from the group consisting of a linear alkylene group which has 1 to 30 carbon atoms and may have a substituent and a group in which one or two or more non-adjacent $-CH_2-$'s are substituted by $-O-$, $-S-$, $-C(=O)-$, $-OC(=O)-$, $-C(=O)O-$, $-OC(=O)O-$, $-NR_{201}C(=O)-$, $-C(=O)NR_{202}-$, $-OC(=O)NR_{203}-$, $-NR_{204}C(=O)O-$, $-SC(=O)-$, or $-C(=O)S-$ in the linear alkylene group which has 1 to 30 carbon atoms and may have a substituent, where $R_{201}$, $R_{202}$, $R_{203}$, and $R_{204}$ each independently represents $-Sp_4-Pol_4$ or a halogen atom, $Sp_3$ and $Sp_4$ each independently represents a single bond or a divalent linking group, $Pol_1$, $Pol_2$, $Pol_3$, and $Pol_4$ each independently represents a hydrogen atom or a polymerizable group, and the compound represented by Formula 1 has at least one polymerizable group.

2. The compound according to claim 1, wherein Ar is any group represented by Formulas 2-1 to 2-3.

3. The compound according to claim 1, wherein both $L_1$ and $L_2$ are $-O-$, $-OC(=O)-$, $-OC(=O)O-$, or $-O-C(=O)NH-$.

4. The compound according to claim 3, wherein $Sp_1$ and $Sp_2$ each independently represents the linking group.

5. The compound according to claim 1, wherein $Pol_1-Sp_1-L_1-$ and $Pol_2-Sp_2-L_2-$ are the same.

6. The compound according to claim 1, wherein all the polymerizable groups are (meth)acryloyloxy groups.

7. The compound according to claim 1, wherein the compound represented by Formula 1 has at least two polymerizable groups.

8. The compound according to claim 1 represented by the following formula:
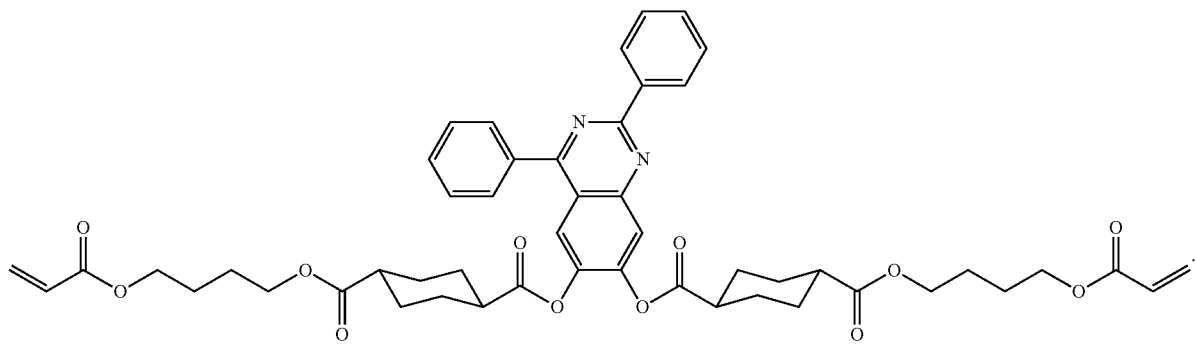
(VI-2)
9. The compound according to claim 1 represented by any one of the following formulae:
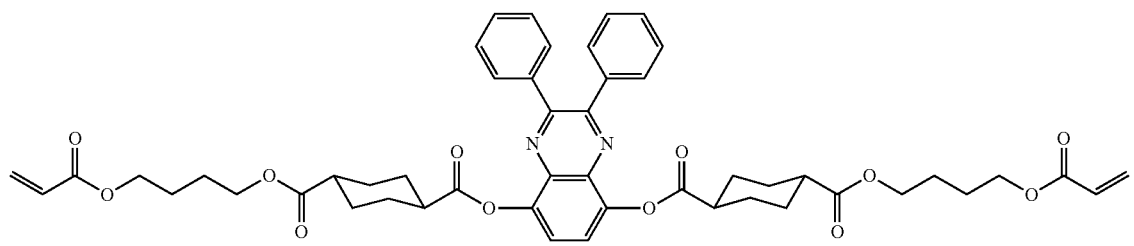
(VI-1)
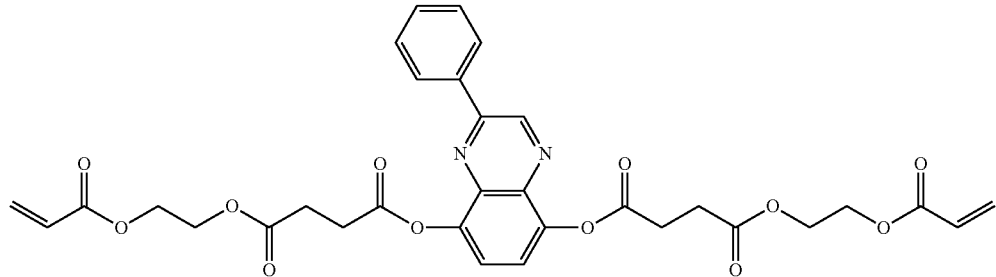
(III-21)
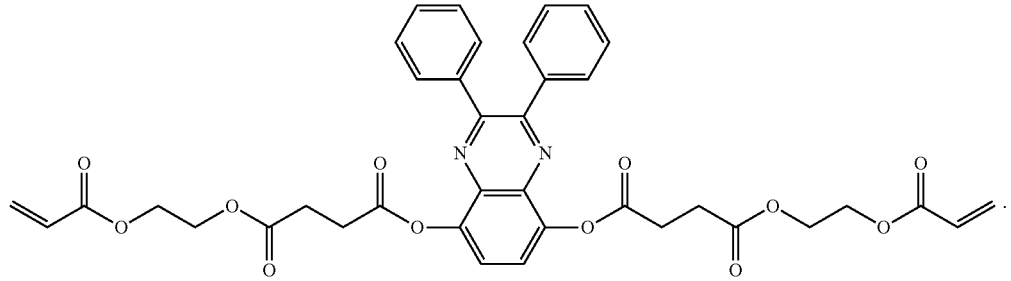
(III-1)